(12) United States Patent
Hossack et al.

(10) Patent No.: US 7,914,458 B2
(45) Date of Patent: Mar. 29, 2011

(54) CAPACITIVE MICROFABRICATED ULTRASOUND TRANSDUCER-BASED INTRAVASCULAR ULTRASOUND PROBES

(75) Inventors: Norman Hugh Hossack, Folsom, CA (US); Blair Walker, Mission Viejo, CA (US); Stephen Charles Davies, Folsom, CA (US); Donald Stanley Mamayek, Mountain View, CA (US); John F. Sheridan, San Diego, CA (US)

(73) Assignee: Volcano Corporation, Rancho Cordova, CA (US)

( * ) Notice: Subject to any disclaimer, the term of this patent is extended or adjusted under 35 U.S.C. 154(b) by 1175 days.

(21) Appl. No.: 11/418,793

(22) Filed: May 5, 2006

(65) Prior Publication Data

US 2006/0264758 A1   Nov. 23, 2006

Related U.S. Application Data

(60) Provisional application No. 60/677,876, filed on May 5, 2005.

(51) Int. Cl.
*A61B 8/14* (2006.01)
(52) U.S. Cl. ........ 600/466; 600/437; 600/459; 600/462; 600/463; 600/467; 600/472
(58) Field of Classification Search ................. 600/437, 600/459, 462, 463, 466, 467, 472
See application file for complete search history.

(56) References Cited

U.S. PATENT DOCUMENTS

| | | |
|---|---|---|
| 4,194,510 A | 3/1980 | Proudian |
| 5,176,141 A | 1/1993 | Bom et al. |
| 5,240,003 A | 8/1993 | Lancee et al. |
| 5,577,506 A * | 11/1996 | Dias ............................ 600/459 |
| 5,606,975 A | 3/1997 | Liang et al. |
| 5,651,366 A | 7/1997 | Liang et al. |
| 6,027,450 A | 2/2000 | Brown et al. |
| 6,475,149 B1 | 11/2002 | Sumanaweera |
| 6,499,348 B1 | 12/2002 | Mamayek |
| 6,537,220 B1 | 3/2003 | Friemel et al. |
| 6,558,330 B1 | 5/2003 | Ayter et al. |
| 6,562,650 B2 | 5/2003 | Ladabaum |
| 6,605,043 B1 | 8/2003 | Dreschel et al. |
| 6,712,767 B2 | 3/2004 | Hossack et al. |
| 6,795,374 B2 | 9/2004 | Barnes et al. |
| 6,875,176 B2 | 4/2005 | Mourad et al. |
| 7,022,077 B2 | 4/2006 | Mourad et al. |

(Continued)

OTHER PUBLICATIONS

Cittadine, A., Erskine, H., "Tiny Chip Big Impact: The Next Wave of Ultrasound", RT Image, Jan. 19, 2004, pp. 24-28, vol. 17, No. 3, Valley Forge Publishing Group, Norristown, U.S.A.

(Continued)

*Primary Examiner* — Brian Casler
*Assistant Examiner* — James Kish
(74) *Attorney, Agent, or Firm* — Haynes and Boone LLP

(57) ABSTRACT

An ultrasound catheter is described herein for insertion into a cavity such as a blood vessel to facilitate imaging within a vasculature. The catheter comprises an elongate flexible shaft, a capacitive microfabricated ultrasonic transducer, and a sonic reflector. The elongate flexible shaft has a proximate end and a distal end. A capacitive microfabricated ultrasonic transducer (cMUT) is mounted to the shaft near the distal end. The reflector is positioned such that a reflective surface redirects ultrasonic waves to and from the transducer. In other embodiments, the catheter comprises a plurality of cMUT elements and operates without the use of reflectors. In further embodiments, integrated circuitry is incorporated into the design.

26 Claims, 28 Drawing Sheets

U.S. PATENT DOCUMENTS

| | | | |
|---|---|---|---|
| 7,077,808 B2 * | 7/2006 | Couvillon, Jr. | 600/466 |
| 2003/0018255 A1 | 1/2003 | Martin | |
| 2004/0015065 A1 | 1/2004 | Panescu et al. | |
| 2004/0160144 A1 | 8/2004 | Daft et al. | |
| 2004/0236223 A1 | 11/2004 | Barnes et al. | |
| 2004/0267134 A1 | 12/2004 | Hossack et al. | |
| 2005/0121734 A1 | 6/2005 | Degertekin et al. | |
| 2005/0177045 A1 * | 8/2005 | Degertekin et al. | 600/457 |
| 2005/0203409 A1 * | 9/2005 | Frey et al. | 600/459 |
| 2006/0084875 A1 | 4/2006 | Knight | |

OTHER PUBLICATIONS

Degertekin, F. L., Guldiken, R., Karaman, M., "Annular-Ring CMUT Arrays for Forward-Looking IVUS: Transducer Characterization and Imaging", IEEE Transactions on Ultrasonics, Ferroelectrics, and Frequency Control, Feb. 2006, pp. 474-482, vol. 53, No. 2, Institute of Electrical and Electronics Engineers, New York, U.S.A.

Demirci, U., Ergun, A., Oralkan, Ö., Karaman, M., Khuri-Yakub, B., "Forward-Viewing CMUT Arrays for Medical Imaging", IEEE Transactions on Ultrasonics, Ferroelectrics, and Frequency Control, Jul. 2004, pp. 886-894, vol. 51, No. 7, Institute of Electrical and Electronics Engineers, New York, U.S.A.

Oralkan, Ö., Ergun, A. S., Johnson, J., Karaman, M., Demirci, U., Kaviani, K., Lee, T., Khuri-Yakub, B., "Capacitive Micromachined Ultrasonic Transducers: Next-Generation Arrays for Acoustic Imaging?", IEEE Transactions on Ultrasonics, Ferroelectrics, and Frequency Control, Nov. 2002, pp. 1596-1610, vol. 19, No. 11, Institute of Electrical and Electronics Engineers, New York, U.S.A.

Wang, Y., Stephens, D., O'Donnell, M., "Optimizing the Beam Pattern of a Forward-Viewing Ring-Annular Ultrasound Array for Intravascular Imaging", IEEE Transactions on Ultrasonics, Ferroelectrics, and Frequency Control, Dec. 2002, pp. 1652-1664, vol. 49, No. 12, Institute of Electrical and Electronics Engineers, New York, U.S.A.

International Search Report dated Jul. 13, 2007 for PCT/US06/17401.

Written Opinion Of International Searching Authority for PCT/US06/17401; dated Jul. 13, 2007.

* cited by examiner

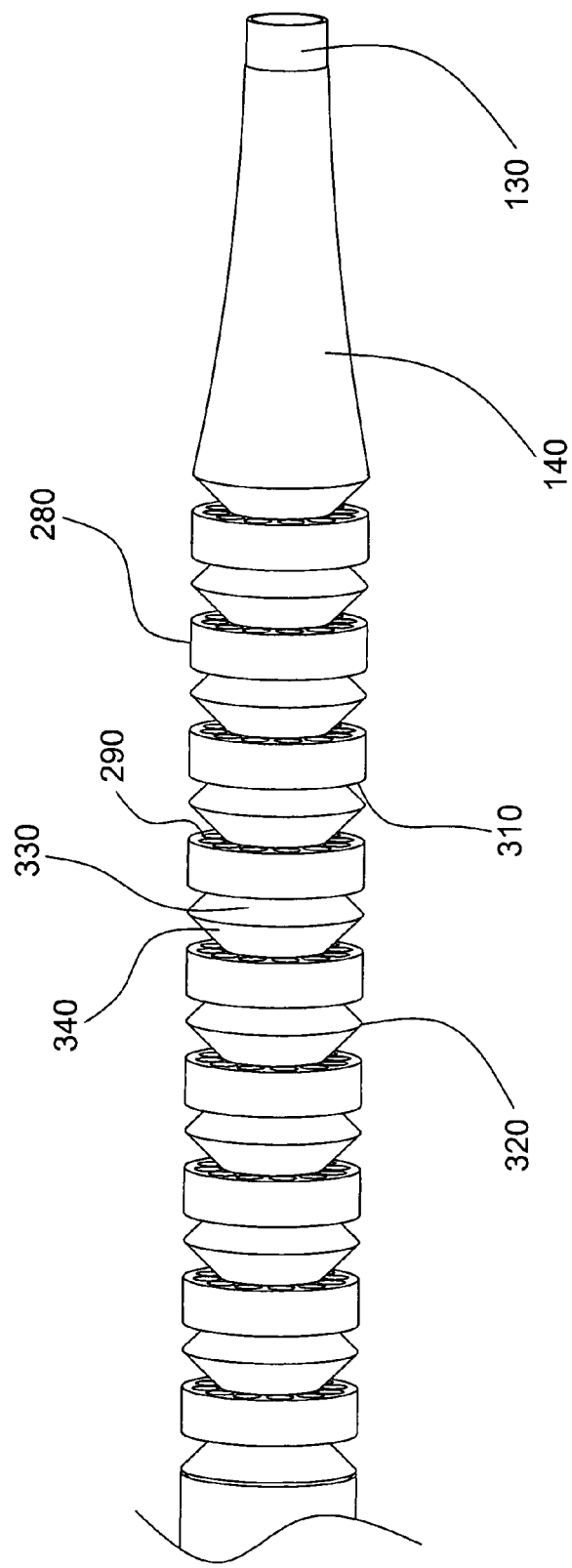

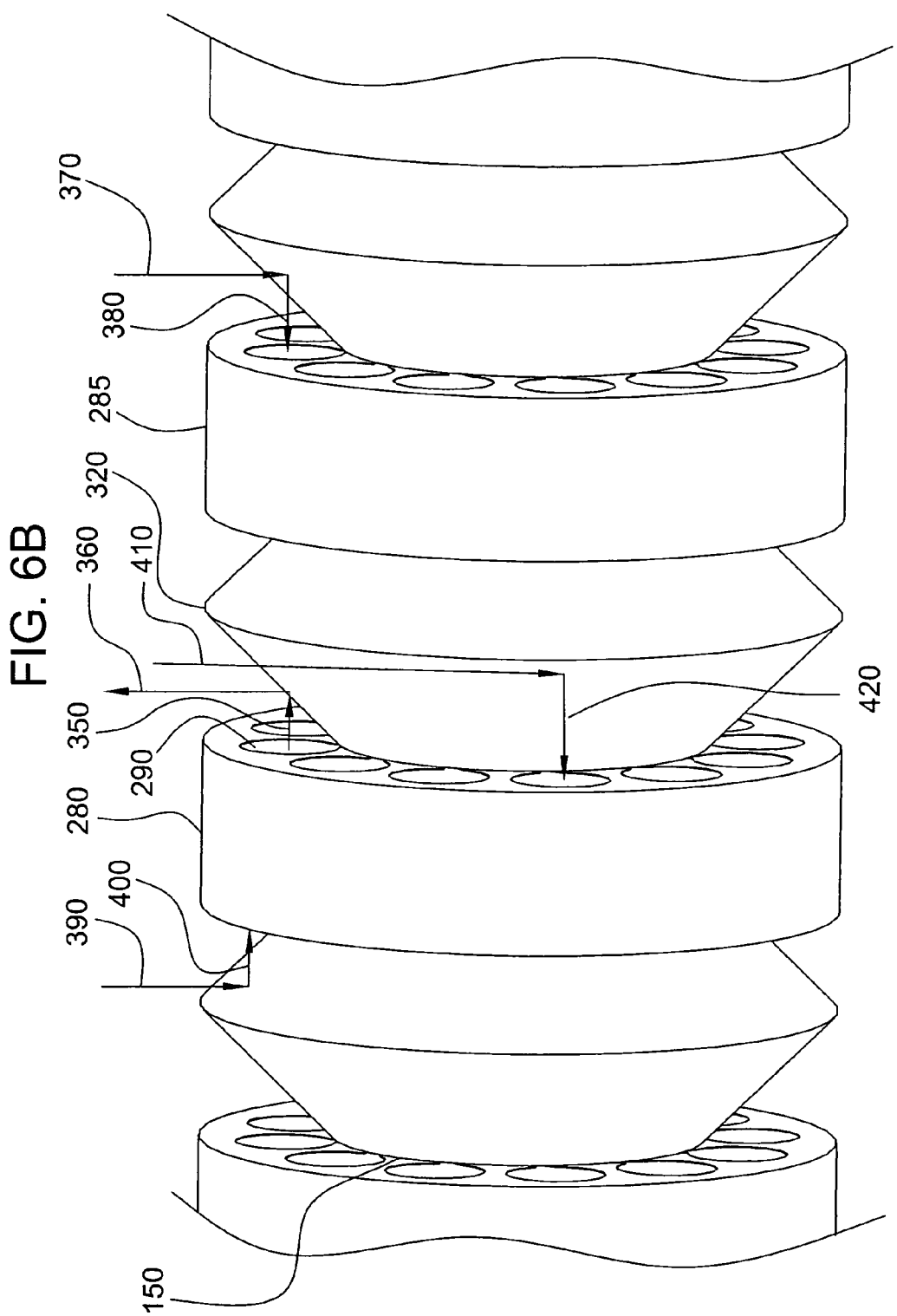

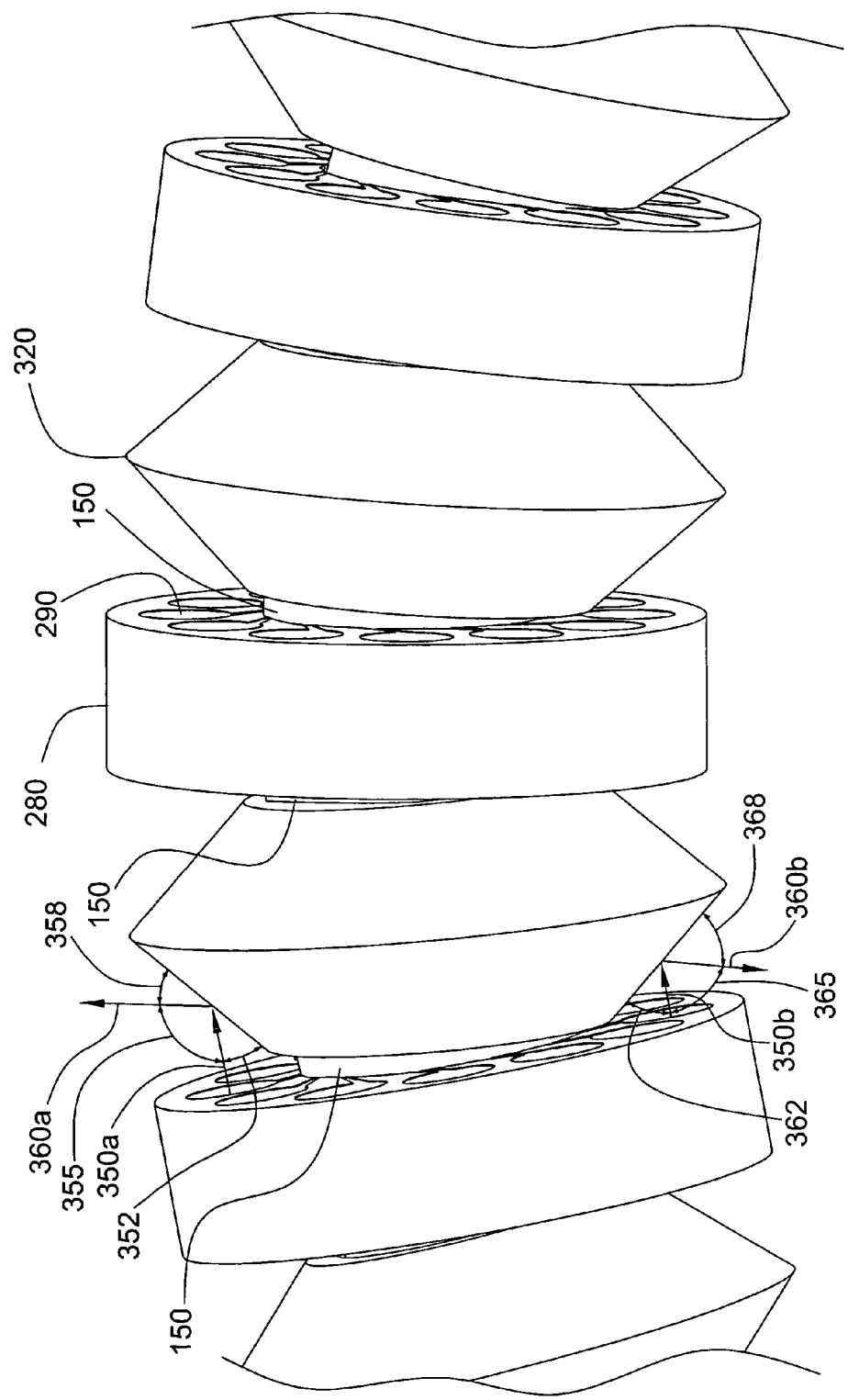

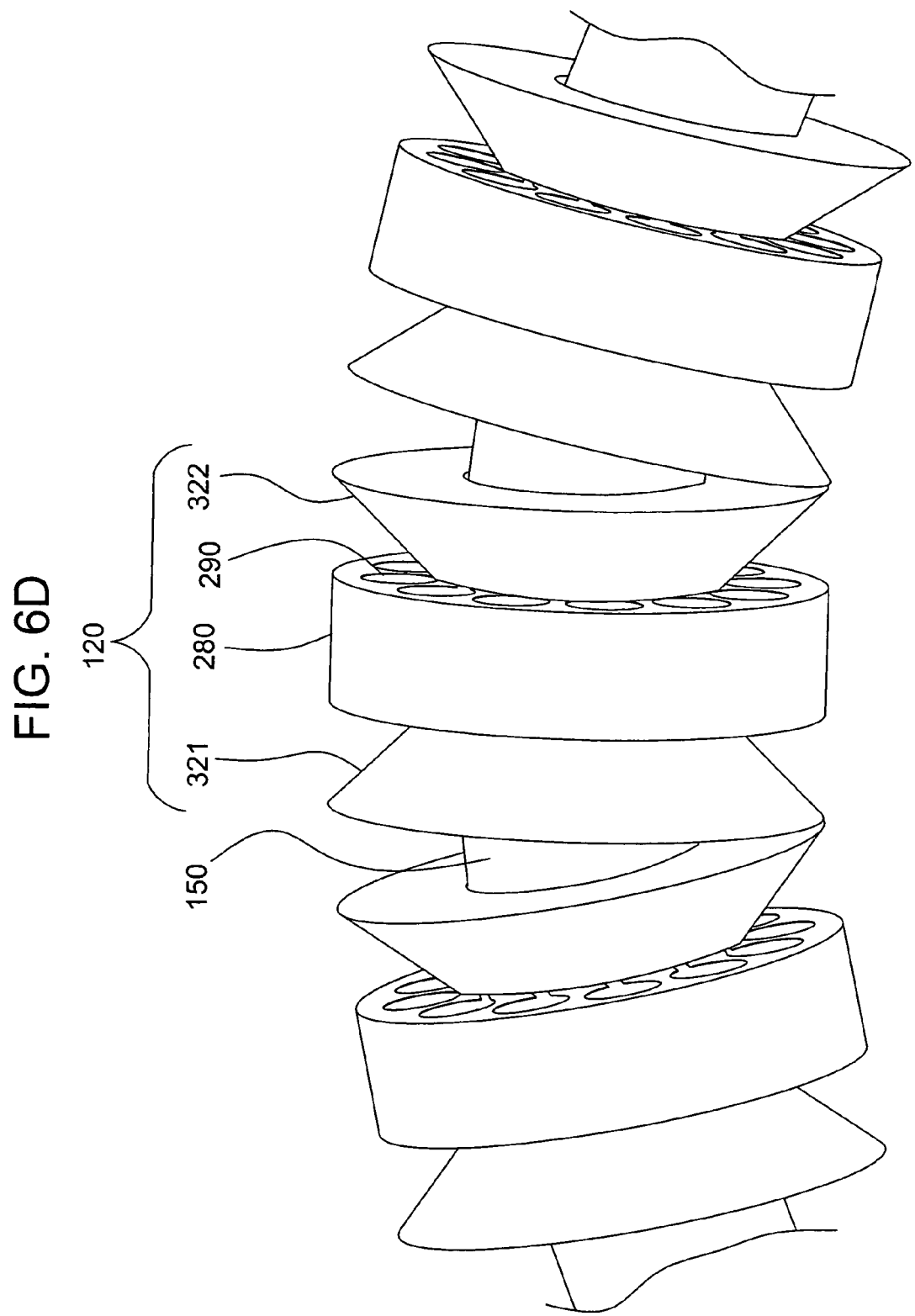

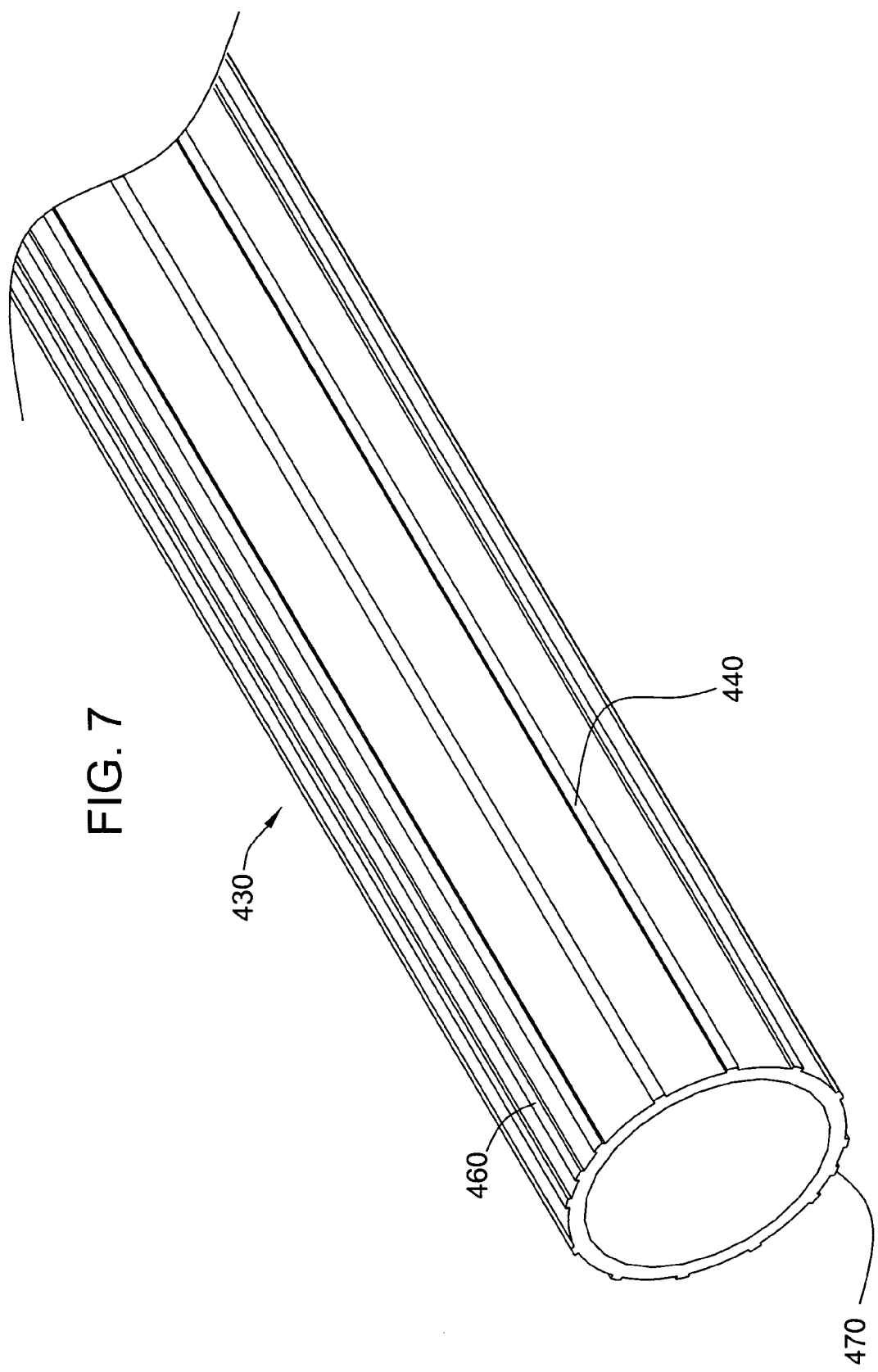

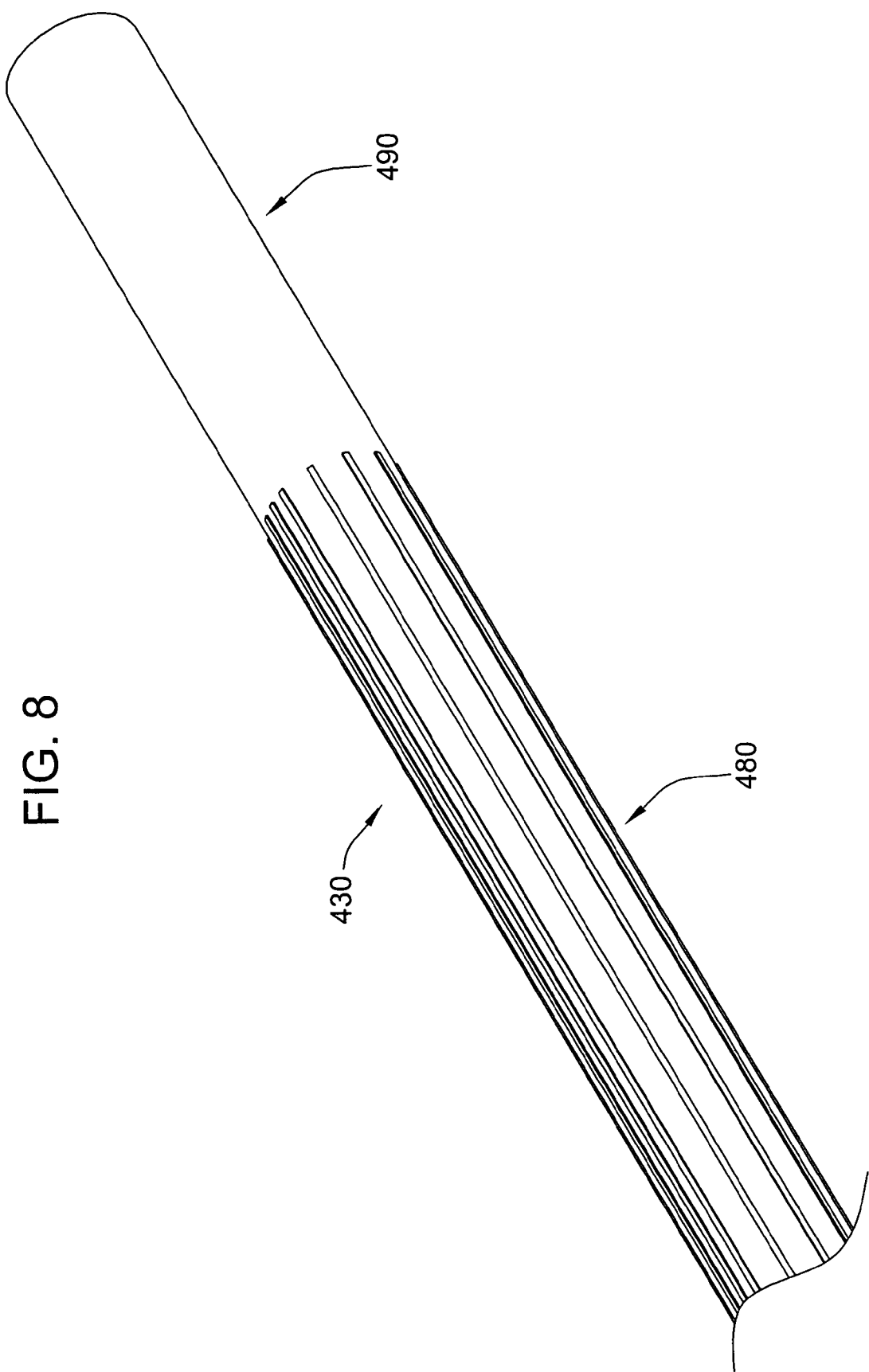

CAPACITIVE MICROFABRICATED ULTRASOUND TRANSDUCER-BASED INTRAVASCULAR ULTRASOUND PROBES

CROSS-REFERENCE TO RELATED APPLICATION

This application claims priority of Hossack et al. U.S. provisional application Ser. No. 60/677,876 filed on May 5, 2005, entitled "cMUT IVUS CATHETERS," the contents of which are expressly incorporated herein by reference in their entirety including the contents and teachings of any references contained therein.

BACKGROUND OF THE INVENTION

Intravascular Ultrasound (IVUS) has become an important interventional diagnostic procedure for imaging atherosclerosis and other vessel diseases and defects. In the procedure, an IVUS catheter is threaded over a guidewire into a blood vessel of interest, and images are acquired of the atherosclerotic plaque and surrounding area using ultrasonic echoes. This information is much more descriptive than the traditional standard of angiography, which only shows an image of the blood flowing through the vessel lumen. Some of the key applications of IVUS include: determining a correct diameter and length of a stent to choose for dilating an arterial stenosis, verifying that a post-stenting diameter and luminal cross-section area are adequate, verifying that a stent is well apposed against a vessel wall to minimize thrombosis and optimize drug delivery (in the case of a drug eluting stent) and identifying an exact location of side-branch vessels. In addition, new techniques such as virtual histology (RF signal-based tissue characterization) show promise of aiding identification of vulnerable plaque (i.e., plaque which is prone to rupture and lead to onset of a heart attack).

There are generally two standard types of IVUS catheters, rotational IVUS catheters and phased array catheters. In a rotational IVUS catheter, a single transducer consisting of a piezoelectric crystal is rotated at approximately 1800 revolutions per minute while the element is excited by a signal. This causes the element to vibrate at a frequency from around 9 to 45 MHz, and above depending on the dimensions and characteristics of the transducer. The single element transducer of the rotational IVUS catheter can be made very thin and therefore able to vibrate at relatively high frequencies, thus achieving a relatively high resolution, especially in the near field (close to the outside diameter of the catheter sheath). In addition, this type of transducer can be excited by a relatively high Voltage, increasing the signal to noise ratio. Because the transducer rotationally sweeps past the guidewire during each rotation, a guidewire shadow is seen in the image that obscures some of the image of tissue in back of the guidewire. In addition, rotation of the transducer, usually achieved by a reinforced coil drive shaft, can be uneven and cause distortion of the image. This effect is known as NURD (non-uniform rotational distortion).

Another type of IVUS catheter is a phased array (or solid state) catheter. This catheter has no rotating parts, but instead has a multi-element transducer (for example 64 elements), in which each element is fired in a specific order by means of several small integrated circuits in the tip of the catheter. The multiplexing and demultiplexing performed by the integrated circuits allows for a minimal number of wires inside the catheter. Due to its structure, this type of catheter requires little or no prepping (e.g. flushing with saline to remove air bubbles from within the catheter) and is very flexible and trackable over a guidewire. It is a difficult, multi-step process to make this multi element transducer. One of the challenges of this method is that it is difficult to make the elements thin enough to achieve frequencies as high as those utilized in rotational IVUS catheters.

In the last decade, a new technology has shown promise in ultrasound transducers. This technology is known as cMUT (capacitive Microfabricated Ultrasonic Transducer). The cMUT transducers typically consist of an array of tiny drums fabricated on silicon or other semi-conductor materials. In the cMUT manufacturing process, a thin sacrificial layer is first deposited in a desired pattern. A thin nitride layer is then deposited over the sacrificial layer. This will form both the "drum shell" (bottom and cylinder) and the "drum head" (membrane). Tiny holes are etched through the nitride layer, allowing the sacrificial layer to be removed. The nitride layer is then sealed and an electrical connection is made, so that the membrane can be excited, causing it to vibrate. Typically, a bias DC Voltage is applied to keep the drum from collapsing. New techniques, however, apply the DC bias Voltage to maintain the membrane in a controlled, imploded (or collapsed) state. An AC Voltage is also applied to create the ultrasound energy by inducing vibration within the drum head (membrane). In addition, signal processing circuitry can be included in the silicon base of the cMUT structure. The cMUT transducer shows promise for lower cost fabrication because of the consistency of semiconductor processing technology.

BRIEF SUMMARY OF THE INVENTION

An ultrasound catheter is disclosed herein for insertion into a body cavity, such as a blood vessel. The catheter comprises an elongate flexible shaft, a capacitive microfabricated ultrasonic transducer, and a sonic reflector. The elongate flexible shaft has a proximal end and a distal end. The capacitive microfabricated ultrasonic transducer is mounted to the shaft near the distal end. The reflector is positioned such that a reflective surface redirects ultrasonic waves to and from the transducer. Particular embodiments do not include the reflector, and instead transmit and receive ultrasound signals directly into an imaged medium.

In a disclosed embodiment, the ultrasound catheter comprises an elongate flexible shaft and a probe, mounted upon the flexible shaft, comprising a plurality of capacitive microfabricated ultrasonic transducers. The elongate flexible shaft has a proximal end and a distal end. The plurality of capacitive microfabricated ultrasonic transducers is coupled to the shaft near the distal end.

In yet another disclosed embodiment, the ultrasound catheter comprises an elongate flexible shaft, a capacitive microfabricated ultrasonic transducer, and an integrated circuit. The elongate flexible shaft has a proximal end and a distal end. The capacitive microfabricated ultrasonic transducer module is mounted to the shaft near the distal end. The integrated circuit, interposed between a connector at the proximal end and the cMUT devices at the distal end, performs at least a multiplexing function with regard to signal lines from elements of the transducer module.

BRIEF DESCRIPTION OF THE DRAWINGS

FIG. 6A is a fragmentary side view of the reflective cMUT IVUS catheter of FIG. 5;

FIG. 6B is an enlarged fragmentary view of the reflective cMUT IVUS catheter of FIG. 5, showing representative reflections of ultrasound waves by a sonic mirror;

FIG. 6C is another enlarged fragmentary view of the reflective cMUT IVUS catheter of FIG. 5, showing the catheter in a flexed configuration;

FIG. 6D is another enlarged fragmentary view of another embodiment of a reflective cMUT IVUS catheter wherein the sonic mirror is separable into two elements;

FIG. 7 is a fragmentary perspective view of an embodiment of an inner tube of a cMUT IVUS catheter comprising conductive ridges;

FIG. 8 is a fragmentary perspective view if another embodiment of an inner tube of a cMUT IVUS catheter having a non-ridged section;

DETAILED DESCRIPTION OF THE INVENTION

This invention relates to cMUT IVUS devices that are mounted to distal ends of catheters. The cMUT IVUS devices are presented in two different general configurations, reflective and non-reflective. Reflective cMUT IVUS devices contain one or more cMUT rings and one or more sonic mirrors. The ultrasound is generated by the cMUT rings and reflected by the sonic mirrors in desired directions for imaging blood vessels and their disease. Non-reflective cMUT IVUS probes do not have the sonic mirror elements, but rather transmit the ultrasound directly from the cMUT membranes in the desired direction.

Figure 1:
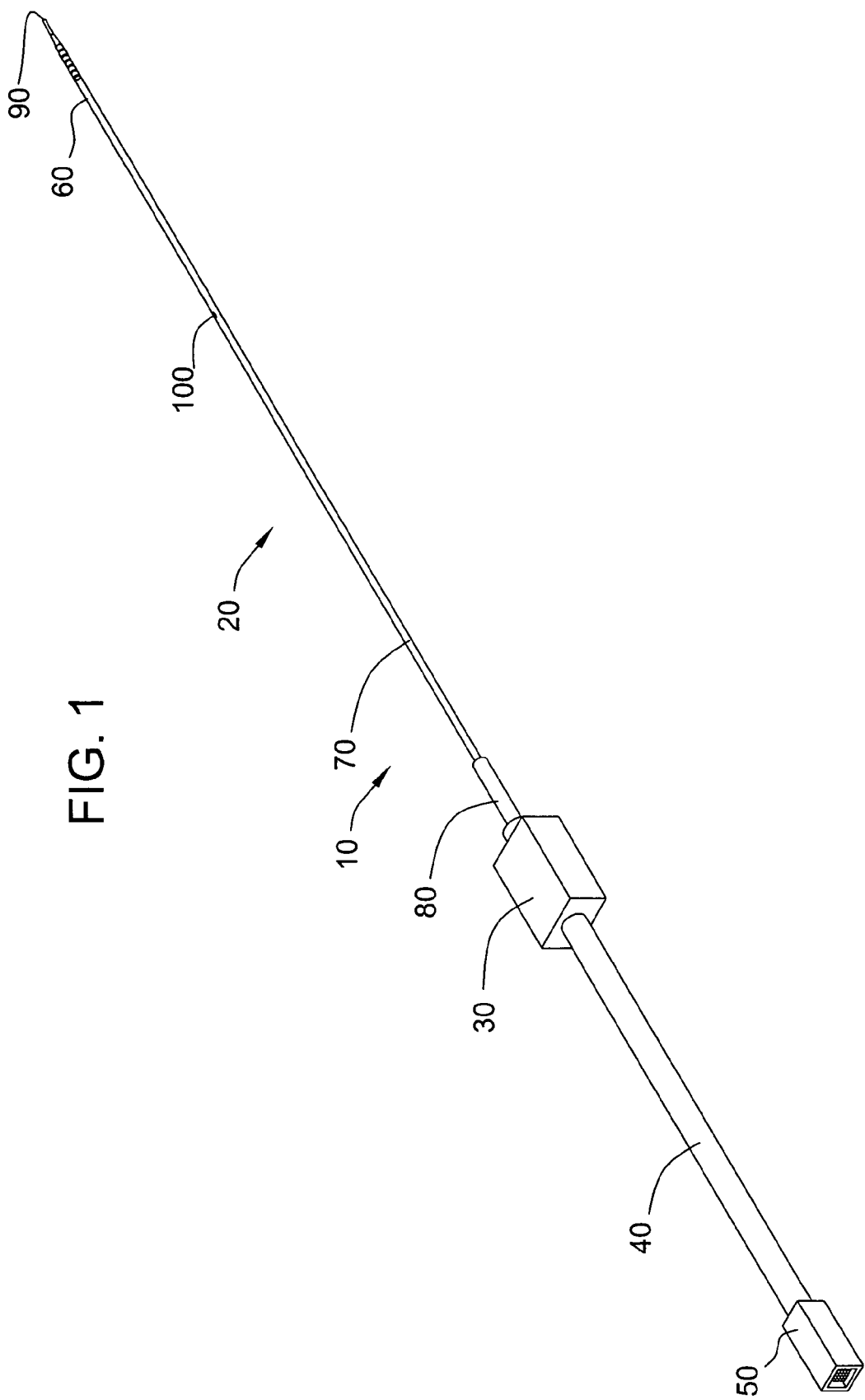
FIG. 1 is a perspective view of a cMUT IVUS catheter.

FIG. 1 shows a cMUT IVUS catheter 10 having a catheter shaft 20, a manifold 30, a cable 40 and an electrical connector 50. The catheter shaft 20 includes a distal end 60 and a proximal end 70. The proximal end 70 includes a strain relief 80. The usable length of the catheter shaft (the portion that can be inserted into a patient) can be varied depending upon the application. For example, in a coronary artery application, a length of 135 cm to 150 cm is desirable. The manifold 30 is an area for transition between the portion of the catheter that is inserted and the portion that remains outside the body. The manifold can also include one or more luer connectors (not shown in this embodiment) to facilitate flushing of the catheter, usually with sterile saline. The distal end 60 of the catheter shaft is the portion which, in the illustrative embodiments, includes the transducers. It is this section that is tracked to the target area in the blood vessel for imaging. Though in some applications, it is not necessary to track the catheter over a guidewire, in most cases, a guidewire lumen is needed in the catheter to allow guidewire tracking of this nature. In the coronary artery application, a preferred guidewire lumen configuration is illustrated in FIG. 1. Though the guidewire is not shown, the guidewire lumen extends from the distal guidewire port 90 to the proximal guidewire port 100. In some embodiments, keeping this length between about 20 cm and 30 cm facilitates a single operator easily advancing/withdrawing the catheter over the guidewire. The proximal guidewire port 100 remains protected inside a separate guiding catheter during the procedure.

In other embodiments of a guidewire lumen, the proximal guidewire port 100 is located at the proximal end of the manifold 30. This configuration allows for exchanges of guidewires during the procedure as well as the ability to flush the lumen. This type of catheter (known as "over-the-wire") may not be as desirable for single operator use as the embodiment pictured in FIG. 1, however, because of the long length of guidewire and catheter engagement that needs to be manipulated outside of the body. It will be appreciated that the catheter and the guidewire may have any suitable length.

Figure 3:
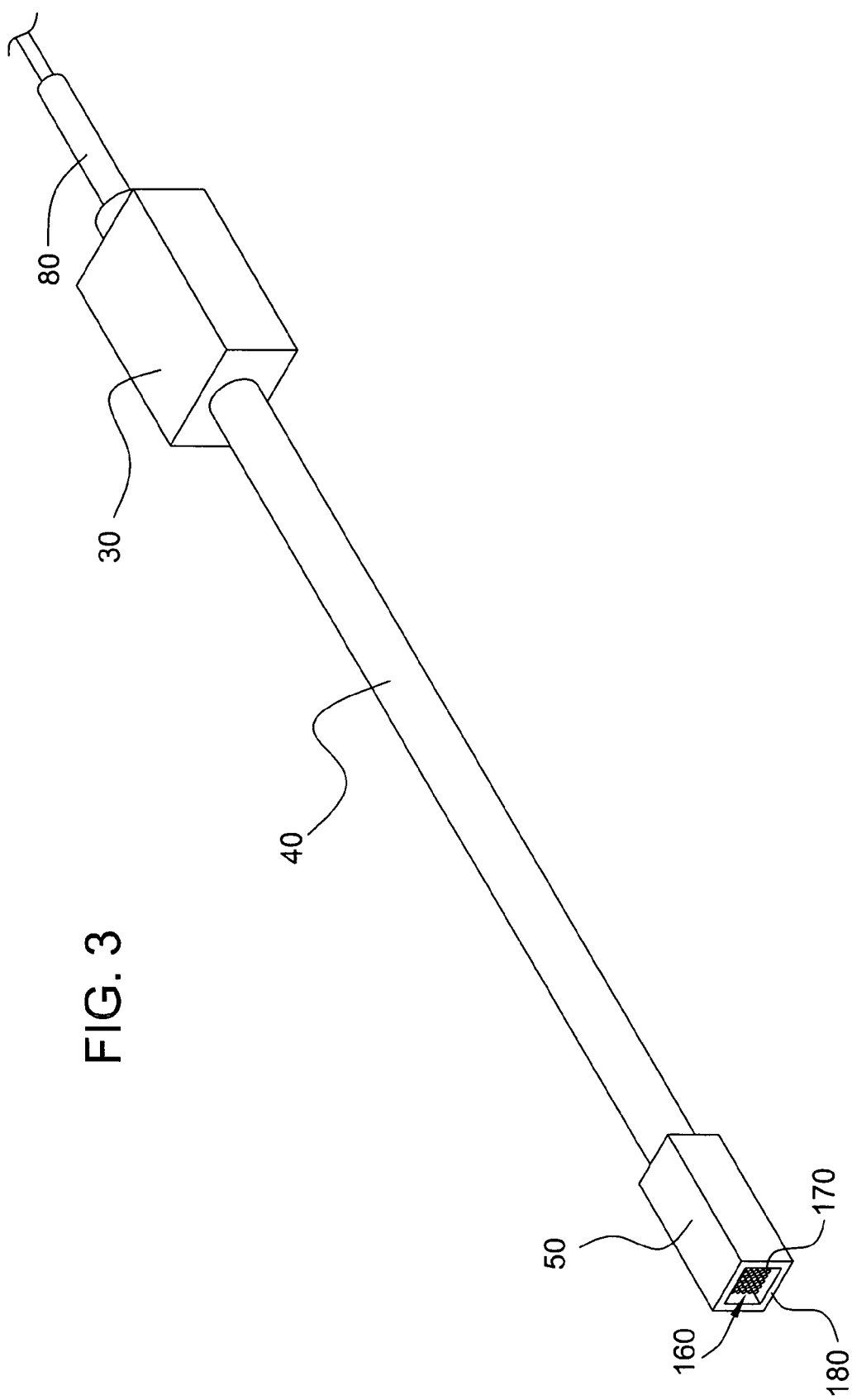
FIG. 3 is another fragmentary perspective view of the cMUT IVUS catheter of FIG. 1.

Referring again to FIG. 1, the electrical connector 50 can be attached to an IVUS console or to a patient interface module, allowing for bi-directional signal transfer. Electrical wires or a flex circuit are contained in the cable 40 to connect the electrical connector 50 with the rest of the catheter 10. Detail of the electrical connector 50 can be seen in FIG. 3. The electrical connector 50 consists of a housing 180 and electrical connections 160, which can consist of a series of one or more pins 170. The connector 50 snaps onto the IVUS console or patient interface module in a frictional and/or locking fashion. The console or patient interface module can be configured to allow more than one of these connectors to attach (e.g., from two different types of catheters).

Figure 2:
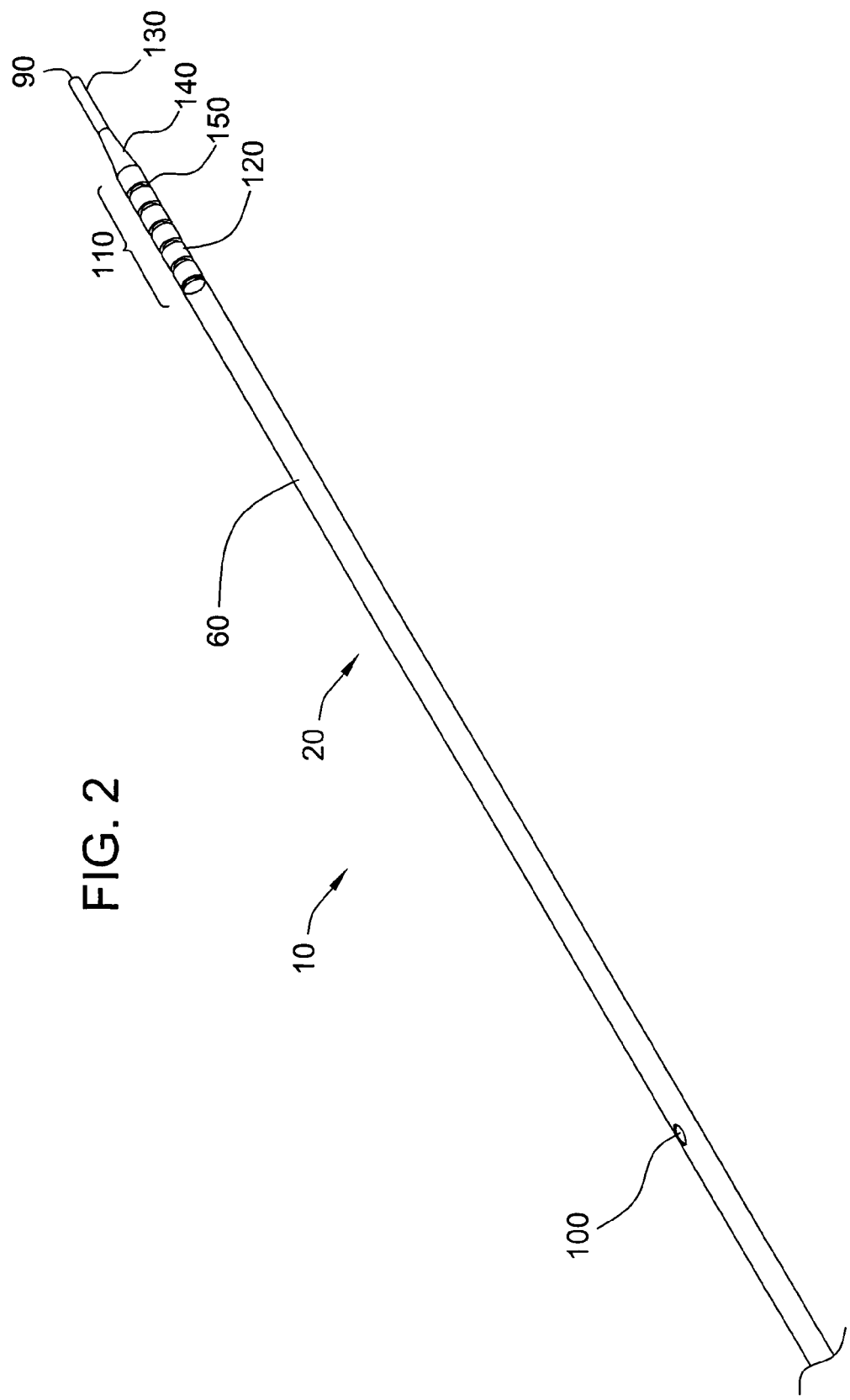
FIG. 2 is a fragmentary perspective view of the cMUT IVUS catheter of FIG. 1.

FIG. 2 shows details of the distal portion of the catheter 10 depicted in FIG. 1. A modular series of capacitive microfabricated ultrasonic transducers (cMUT) 110 having one or more individual modules 120 is disposed at the distal end 60 of the catheter shaft 20. The modules 120 can be configured for side-viewing IVUS, forward-viewing IVUS or a combination of the two in the same catheter. The modular nature of the cMUT series 110 allows for this adaptability and customization and permits greater flexibility and trackability of the catheter due to flex points, e.g., flex point 150 between the individual modules of the cMUT series 110. The diameter of the cross-section of the modules making up the cMUT series 110 is, by way of example, close in size to the diameter of the cross-section of the distal end 60 of the catheter shaft 20. The dimension matching allows for smoother catheter tracking through tight vessel segments. A small diameter distal tip 130 allows the catheter to smoothly enter a severely reduced diameter portion of the diseased vessel over the guidewire, or to track through severe tortuosity. A transition section 140 assures that the step up in diameter between the distal tip 130 and the rest of the distal end 60 is gradual/tapered and not abrupt. The transition section 140 therefore reduces the chances that the catheter will be caught/blocked when navigating through any challenging portions of anatomy, stents or other intravascular devices. This is important in several types of anatomy in which these catheters can be used, including, but not limited to, coronary, carotid, neuro, peripheral or venous.

Figure 4:
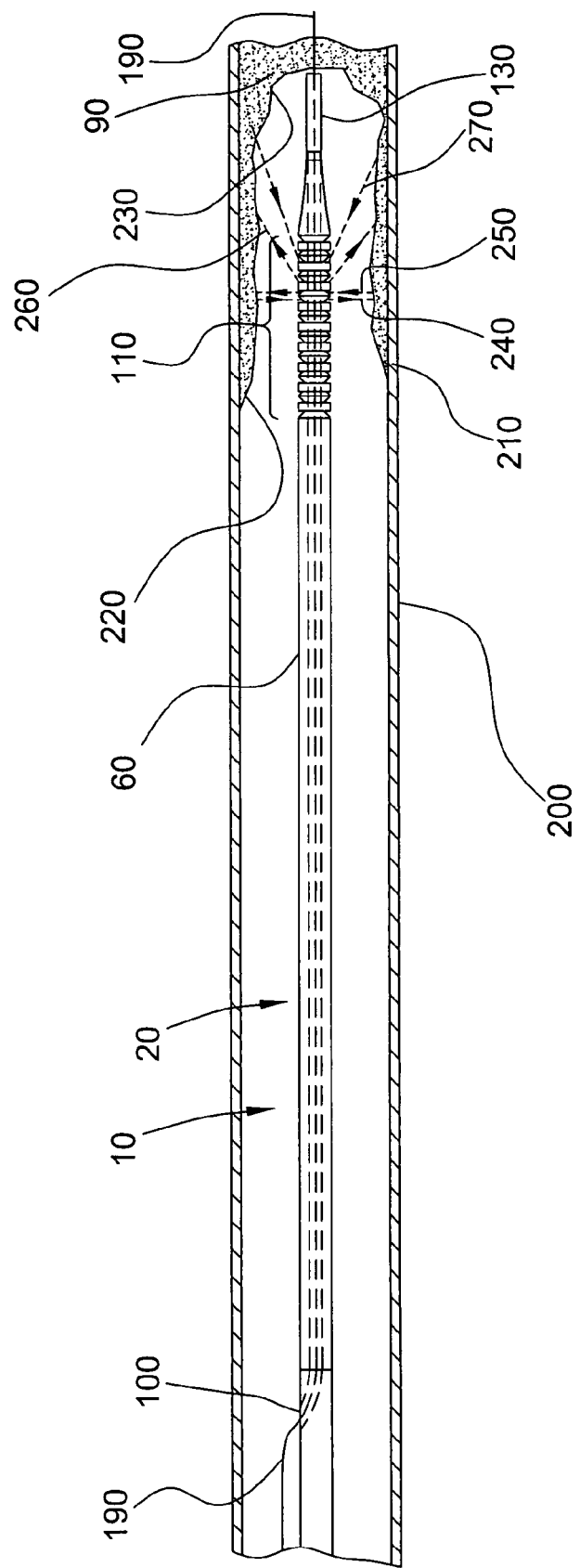
FIG. 4 is a fragmentary partial cross-sectional side view of a cMUT IVUS catheter disposed within a blood vessel.

FIG. 4 illustrates a cMUT IVUS catheter 10 in an operable position over a guidewire 190 in an artery 200. The atherosclerotic plaque 210 has both stenotic disease 220 and occlusive disease 230 in this case. The catheter 10 is shown emitting side-firing ultrasound 240 to image the stenotic disease 220. Acoustic echoes 250 are received which give information about the nature and dimension of the stenotic disease and underlying vessel. Similarly, the occlusive disease 230 is imaged via the forward-firing ultrasound 260 and corresponding acoustic echoes 270.

Figure 5:
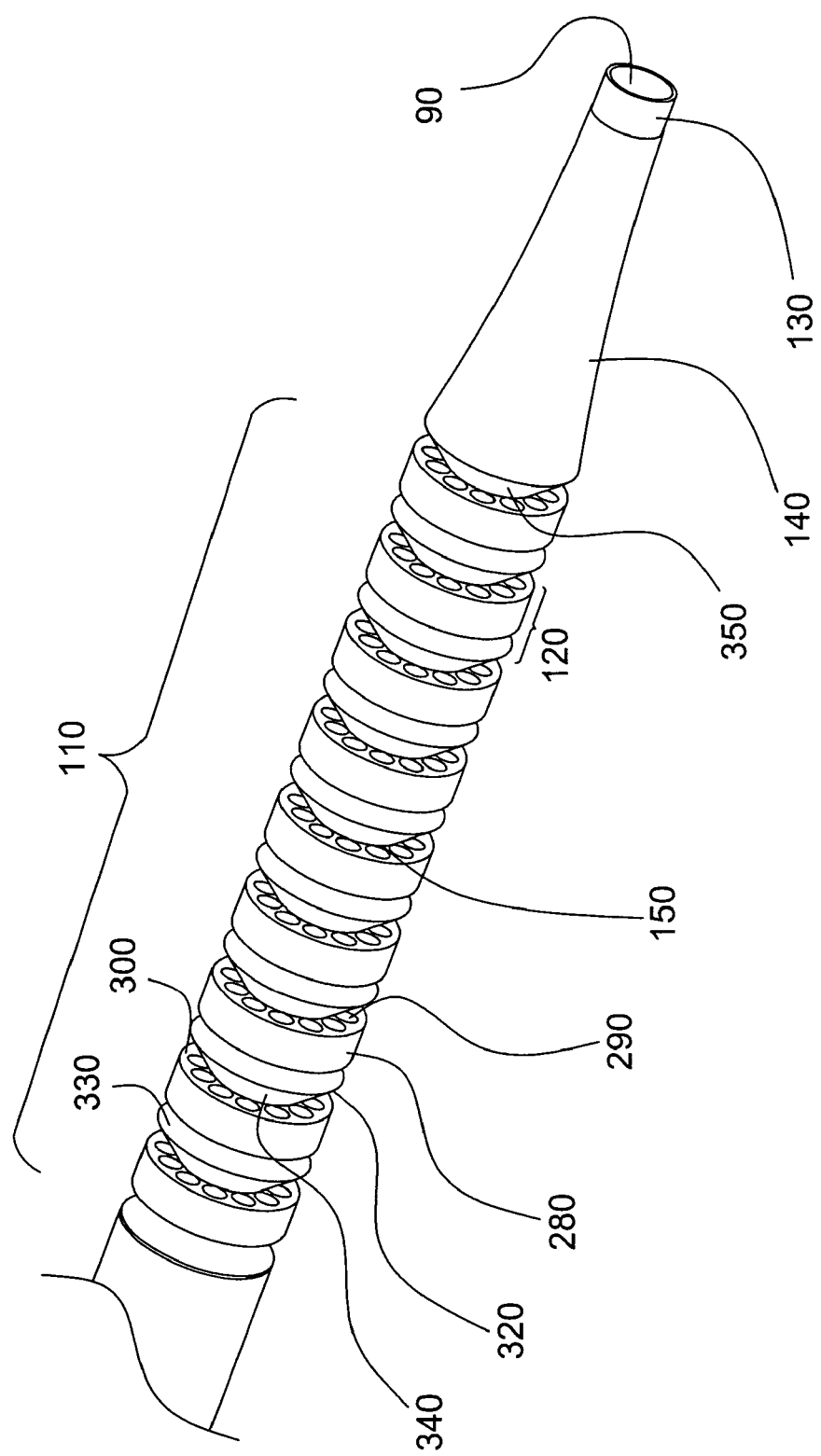
FIG. 5 is a fragmentary perspective view of an embodiment of a reflective cMUT IVUS catheter as viewed from the distal end.

In FIG. 5 and FIG. 6A, two views of the distal end of a first embodiment of a reflective cMUT IVUS catheter are shown. The catheter comprises one or more cMUT rings, such as cMUT ring 280, having a forward face 300 and a backward face 310 (see, FIG. 6A). Thin-walled acoustic membranes, such as membrane 290, are arrayed on each of the two faces of the cMUT ring 280. By way of example, the membranes are substantially circular and have a diameter of about 0.006", but this diameter can be greater or less, depending upon the configuration. Beneath each membrane is a hollow cavity. Interspersed between the cMUT rings are sonic mirrors/reflectors, such as mirror/reflector 320, which serve to reflect the ultrasound and redirect it. The mirrors, by way of example, have an angled front face 330 and an angled back face 340. In the configuration shown in FIGS. 5 and 6a, the faces are angled at 45°. It will be appreciated that the faces may be disposed at any of a variety of suitable angles. The ultrasonic waves emitted in a forward direction by the membranes (e.g., membrane 290) of the forward face 300 are therefore reflected to the side. Similarly, the ultrasonic waves emitted in a backward direction by the membranes of the backward face 310 are reflected to the side. This facilitates a side-viewing IVUS catheter with several modules, such as module 120, made up of a cMUT ring 280 and a sonic mirror 320 combination. While stationary, a catheter of this construction can image over a longer length than the traditional IVUS catheter, which normally would have to be pulled back during the imaging procedure in order to image more than one axial location in a blood vessel.

In the catheter illustrated in FIGS. 5 and 6A, the length of the modular series 110 is approximately six millimeters, however, it will be appreciated that the modular series 110 may be any suitable length and may comprise any suitable number of cMUT rings and mirrors. Over this section there are nine cMUT rings and ten sonic mirrors. Only one of the two faces are used on the distal-most and proximal-most mirrors, the other face of each of those mirrors fitting into a groove inside the transition section and inside the catheter shaft. Therefore, the total number of mirror faces used matches that of the number of cMUT ring sides used: eighteen in this example. This means that over a six millimeter length, there are eighteen axially separated image planes. Each of those image planes is generated by twelve membranes (e.g., membrane 290) of each cMUT ring face. This means that the six millimeter length has a cylindrical array of 18 by 12 elements, or 216 total elements. The "elemental dimensions" of such arrays will differ in accordance with various embodiments.

In existing phased array catheter firing schemes, a single element fires a wavelet. The ensuing/corresponding echo of the wavelet is then sensed by the same element that fired the original wavelet. It is also sensed by several of the neighboring elements. This firing scheme continues for every element, creating what is commonly referred to in the art as a "synthetic aperture." The same sort of firing and receiving strategy is used in the modular series 110 depicted here, both in relation to the circumferential orientation, but also in other orthogonal planes. The width of the cMUT rings and the width of the sonic mirror can be configured so that the axial scan lines have equal spacing.

FIG. 6B depicts the path of an emitted wavelet 350 and a reflected wavelet 360 from the membrane 290 of the cMUT ring 280. The subsequent echoes can be sensed by the same membrane 290, or by other membranes. Examples of the possible membranes are: on the other side of the same ring 280 (echo 390, reflected echo 400), on a different ring 285 (echo 370, reflected echo 380), or in a different circumferential orientation (echo 410, reflected echo 420), or any combination of such side/ring/position alternatives. The circuit control scheme for a cMUT probe device can also be configured so that certain drums only send and other drums only receive. The circuit control scheme can also be configured so that multiple drums fire at the same time. Multiplexing and parallel activation circuitry is, by way of example, configured in the cMUT rings to facilitate each ring to fire and sense echoes at specified times. Likewise, multiplexing and parallel activation circuitry is, by way of example, configured so that selected membranes around the circumference of the ring fire at specified times.

The modular cMUT catheter is, for example, flexible in the imaging region because of the flex points 150 between the modules 120. Turning to FIG. 6C, it is appreciated that as the catheter flexes in the modular section, the flex points 150 allow for a slight separation of the rings and mirrors, thus providing a more flexible and trackable catheter. In other embodiments, the flex points are also in the middle of the module (between a ring/mirror combination). The catheter is shown flexing due to a curve in a blood vessel. The rings and mirror/reflectors at the flex points 150 at the top of FIG. 6C have become more separated, while such separation is not present at the bottom. The incident ultrasound 350a and reflected ultrasound 360a at the top of the figure behave differently from the incident ultrasound 350b and reflected ultrasound 360b at the bottom of the figure. At the bottom of FIG. 6c, an incidence angle 362 of the ultrasonic wave to the sonic mirror face increases, in turn causing the reflectance angle 368 to increase proportionally (in comparison to a catheter in a straight configuration as described above). Also shown is the total angle between incidence and reflectance 365. At the top of FIG. 6C, an incidence angle 352 of an ultrasonic wave to a sonic mirror face decreases, in turn causing a reflectance angle 358 to decrease proportionally. Also shown is a total angle between incidence and reflectance 355. In the figure, angle 355 is greater than angle 365. In a tortuous artery, this effect serves to better maintain the resultant firing of the ultrasonic wave close to perpendicular to the axis of the blood vessel. Another embodiment is presented in FIG. 6D. The sonic mirror is divided into two sections that surround the cMUT ring 280. Proximal sonic mirror 321 and distal sonic mirror 322 provide the reflection of ultrasound waves emanating from the membranes, e.g., membrane 290 of the cMUT ring 280, however they remain static in relation to the cMUT ring so that the incidence and reflectance angles remain constant. The module 120 remains together, and the catheter flexes in the flex points 150 between the modules 120.

In FIGS. 7 and 8, an inner catheter tube 430 is depicted having conductive ridges, e.g., conductive ridge 440. When the inner catheter tube 430 is assembled within the catheter 10, the conductive ridges serve to make electrical connections between the manifold 30 (or the electrical connector 50) and the cMUT devices. The conductive ridges are formed, for example, as bumps in the catheter tubing that are then coated with conductive material, or they can be part of a composite extruded tube. In addition, they can simply be conductive stripes deposited onto the tube 430 by methods known in the art. In the tube 430 depicted in FIGS. 7 and 8, twelve of the conductive ridges deliver an AC signal to a corresponding one of each of twelve circumferentially arrayed membranes within a module. It will be appreciated that any suitable number of signal conductive ridges are used to couple signal sources/sinks to corresponding ones of the cMUT membranes.

A majority of the conductive ridges are used to carry signals corresponding to ultrasound echoes that are created by the cMUT devices. In addition, there is an electrical ground conductive ridge 460 and a DC bias conductive ridge 470. The potential between the ground conductive ridge 460 and the DC bias conductive ridge 470 serves to maintain the cMUT membranes in a desired operational state. The positions/functionality of the various signal/conductive lines corresponding to the ridges differs in accordance with various embodiments. It can be seen in FIG. 8, that the inner tube 430 can have a ridged section 480 and a non-ridged section 490. The non-ridged section 490 has a lower profile, and can be used as the catheter distal tip 130, as depicted in FIG. 2. This also facilitates easier tip bonding during manufacture of the catheter. This is an efficient design because no conductive lines are needed at the very tip of the catheter, distal to the cMUT section, unless there any additional devices needed at the very tip.

Figure 9:
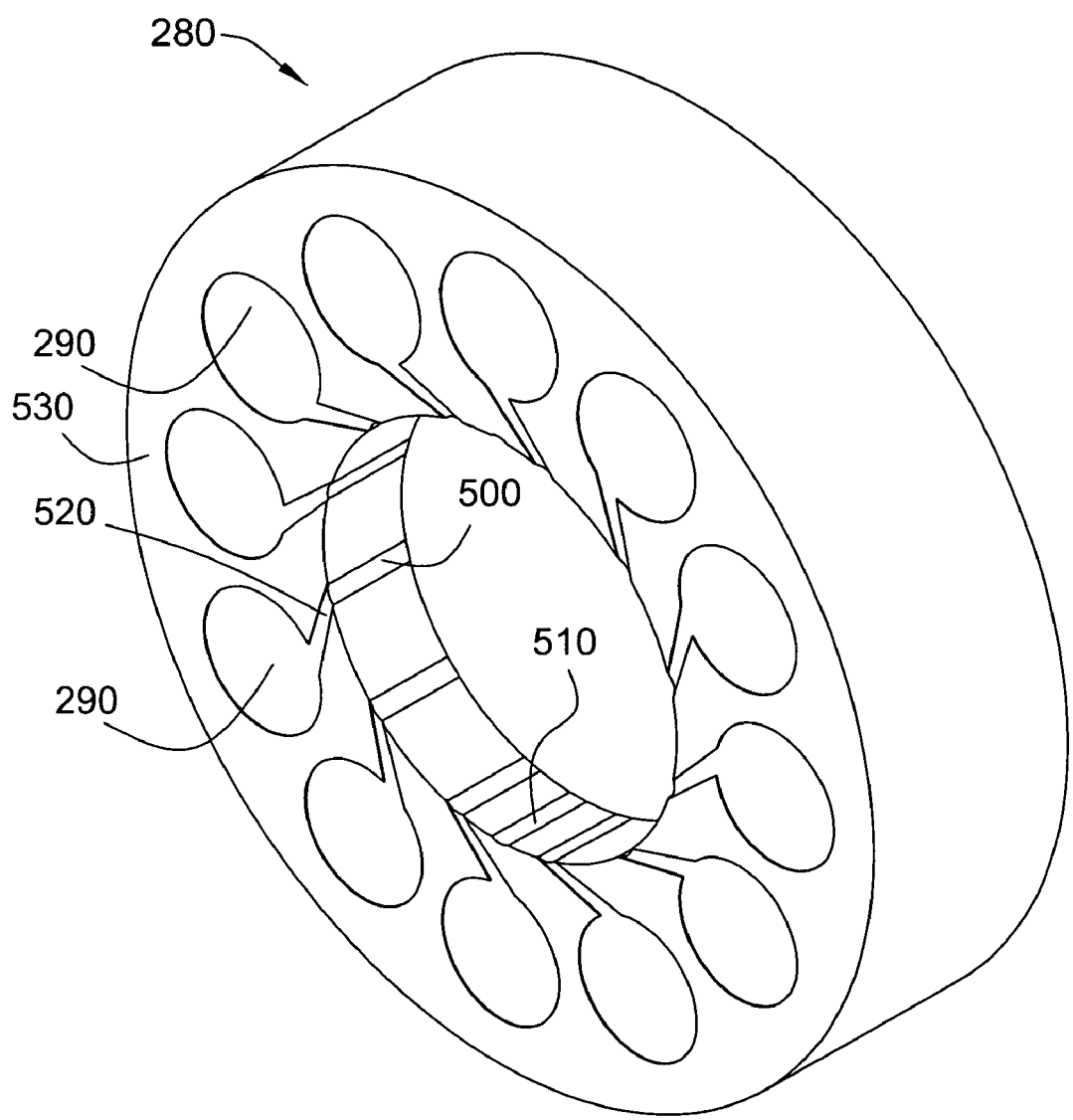
FIG. 9 is a perspective view of a modular cMUT ring.

FIG. 9 shows an exemplary embodiment of conductive pathways to and from a cMUT membrane array of a cMUT ring 280 according to a first embodiment. Membranes, such as membrane 290 are covered with a circular deposition of conductive material. The conductive material, by way of example, is continuous with a conductive path (e.g., path 520 for membrane 290). Preferably, the conductive patterns on a face 530 are deposited in one operation. Continuous with the conductive path 520 is a conductive stripe 500 on the inner wall of the cMUT ring 280. When the ring 280 is attached to the inner tube 430 (see, FIGS. 7 and 8), one of the conductive ridges (e.g., ridge 440) contact, or are conductively bonded to, the conductive stripe 500. This allows a signal sent along the path of a conductive ridge to be electrically coupled to the conductive material on the membrane 290. As depicted in FIG. 9, conductive stripe 5 10 is coupled to either the ground contact of the cMUT ring or the DC bias contact of the cMUT ring.

Figure 10:
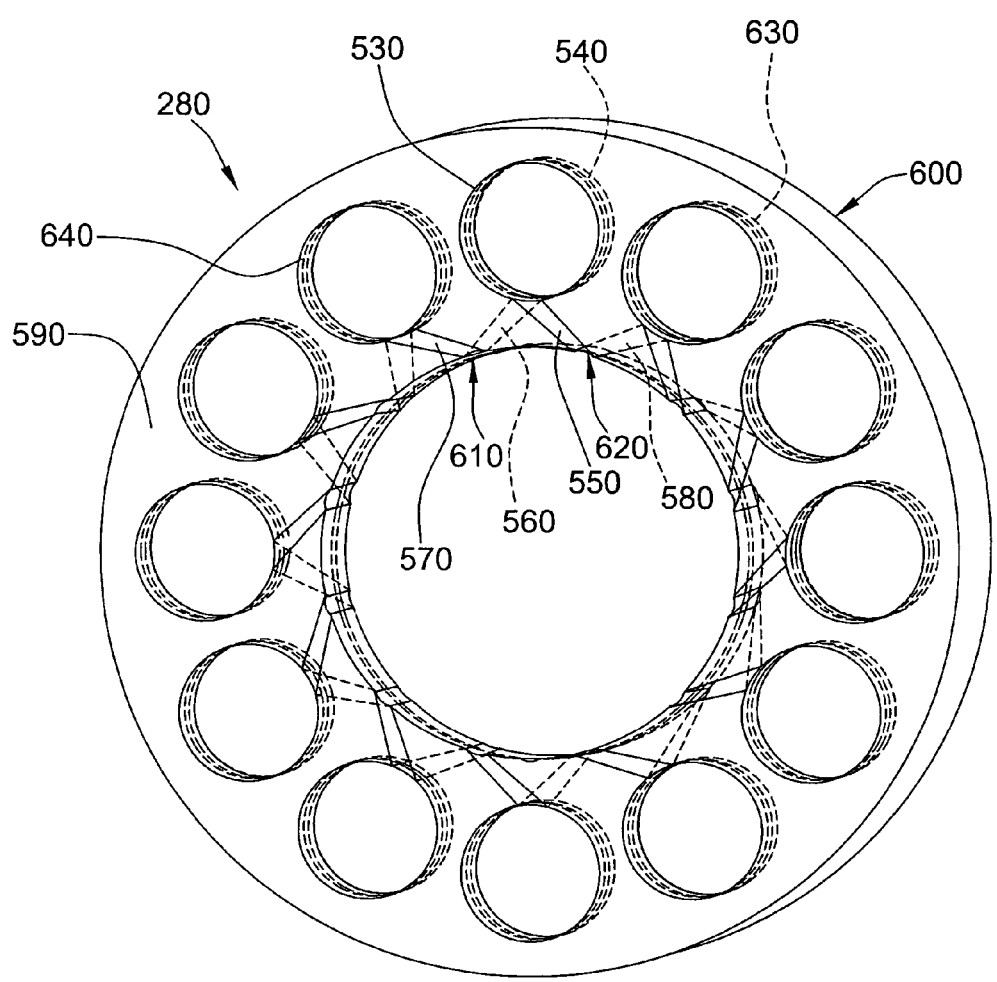
FIG. 10 is another perspective view of the modular cMUT ring of FIG. 9.

FIG. 10 is a semi-transparent view presenting two sides of the cMUT ring 280 of the exemplary embodiment presented in FIG. 9. As depicted, a front facing side 590 has a first conductive path 550 associated with a first membrane 530, and a second conductive path 570 is associated with a second membrane 640. A back facing side 600 has a first membrane 540 associated with a first conductive path 560, and a second conductive path 580 is associated with a second membrane 630. As depicted in FIG. 10, membrane 530 and membrane 540 do not share the same conductive stripe because their respective conductive paths are angled in different directions. For example, the conductive path 550 of membrane 530 shares a conductive stripe 620 with conductive path 580 of a different membrane 630. The conductive path 560 of membrane 540 shares a conductive stripe 610 with the conductive path 570 of a different membrane 640. In this manner, it may be possible to reduce acoustic cross-talk associated with drums on direct opposite sides of the cMUT ring. In other embodiments, the conductive paths associated with membranes on direct opposite sides of the cMUT ring share the same conductive stripe. In yet another embodiment, the drums on one side of the cMUT ring are located at different circumferential angular locations on the ring than the drums on the other side of the ring, for example, skewed 15° out of phase along the opposing surfaces of the ring 280. This may also help to reduce acoustic cross-talk.

Figure 9A:
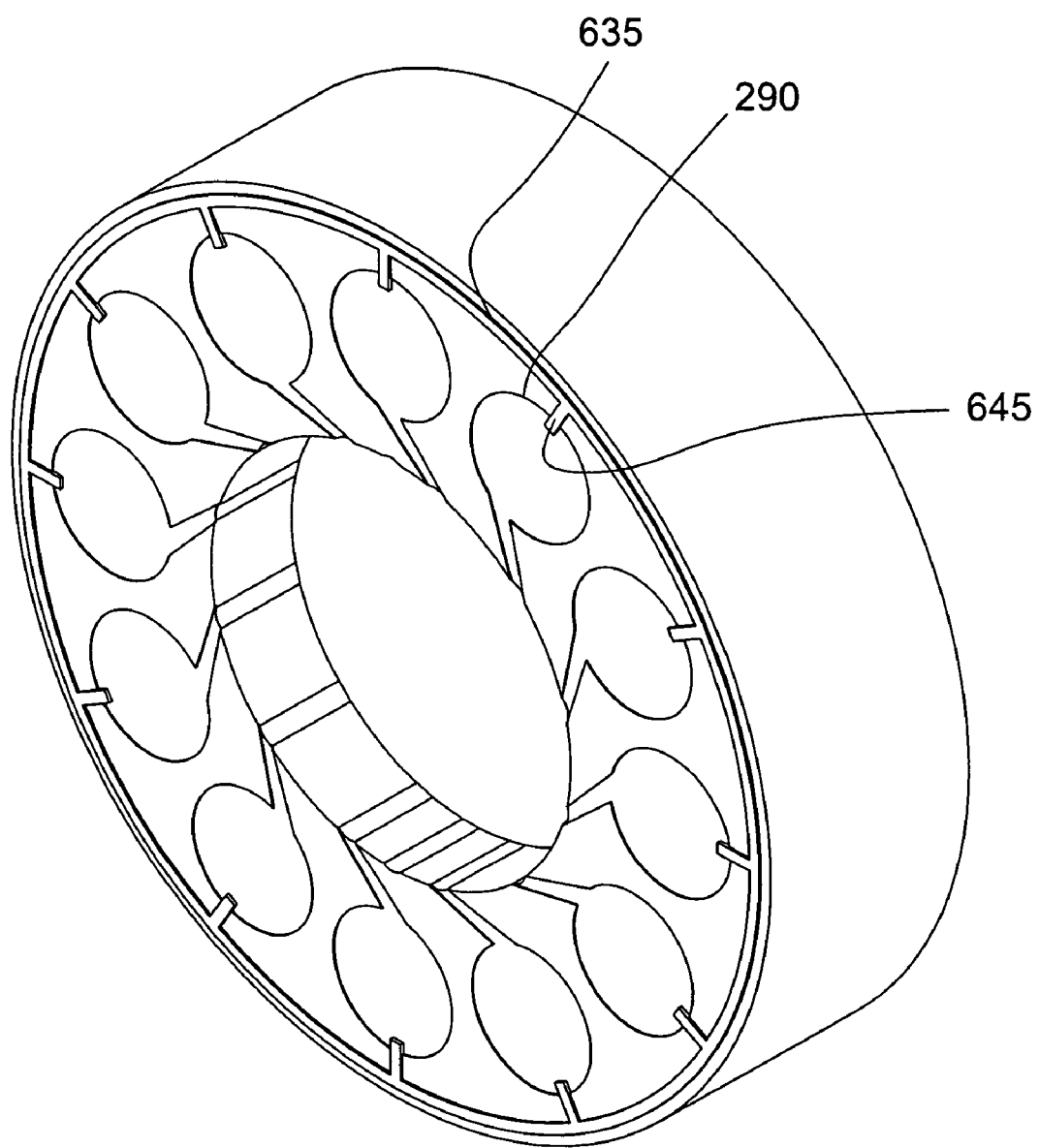
FIG. 9A is a perspective view of another embodiment of a modular cMUT ring with an alternative conductive path arrangement.

FIG. 9A shows a cMUT ring similar to that of FIG. 9, but includes a circumferential conductive stripe 635 that is connected to all of the membranes 290 by individual conductive bridges 645. This illustrates an embodiment suitable for connecting all of the membranes of a face to a single terminal. The signal associated with the single terminal is, by way of example, an electrical ground, a DC bias Voltage or an excitation Voltage, depending upon the configuration. Alternatively, the single terminal is able, for example, to signally communicate with multiple ones of the transducer membranes via the conductive stripes, such as conductive stripe 500 (see, FIG. 9) on the inner wall of the transducer module rings.

Figure 11:
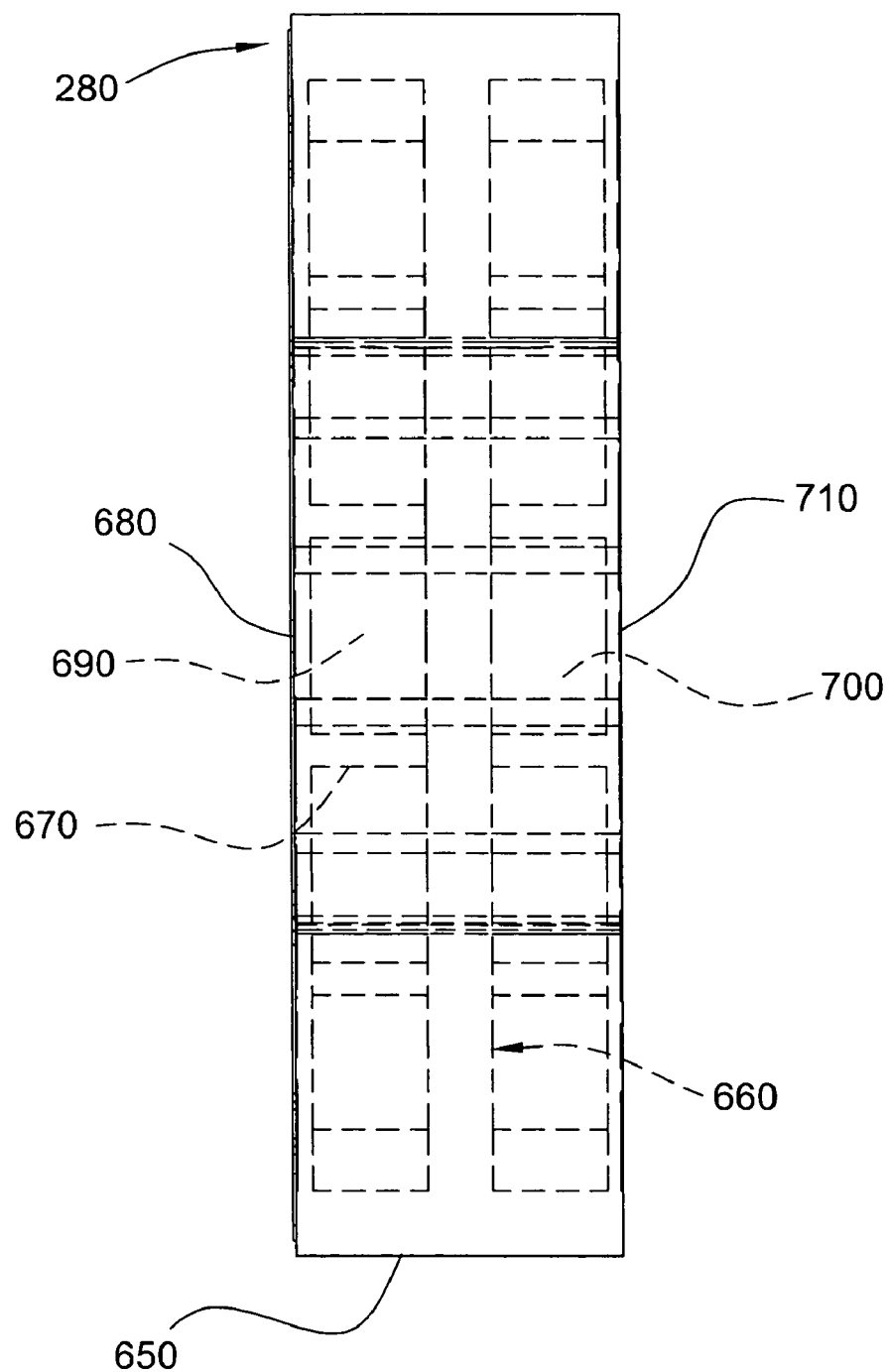
FIG. 11 is a side view of the modular cMUT ring of FIG. 9.

FIG. 11 shows a semi-transparent side view of the exemplary cMUT ring 280, of the embodiment depicted in FIGS. 9 and 10, showing the arrangement of the drums. The cMUT ring 280 is formed, for example, of silicon or other semiconductor material. It will be appreciated that the cMUT ring 280 is constructed of any one of suitable alternative materials. The cMUT ring 280 is two-sided and includes a total of 24 drums, formed by 12 membranes and 12 corresponding cavities on each side. The two sides of the cMUT ring are separated by a common wall 660 which supplies sufficient acoustic isolation so that it minimizes acoustic coupling between any membranes disposed on opposing sides of the ring 280. The common wall 660 forms the bottom of each drum shell. The sides of the drum shells include a combination of the circumferential outer wall 650, a circumferential inner wall (not visible in this longitudinal section) and a series of internal walls, e.g., wall 670. A first drum is depicted on a first side by first cavity 690 and first membrane 680 disposed over the first cavity 690. A second drum is depicted on a second side by a second cavity 700 and a second membrane 710.

Figure 12:
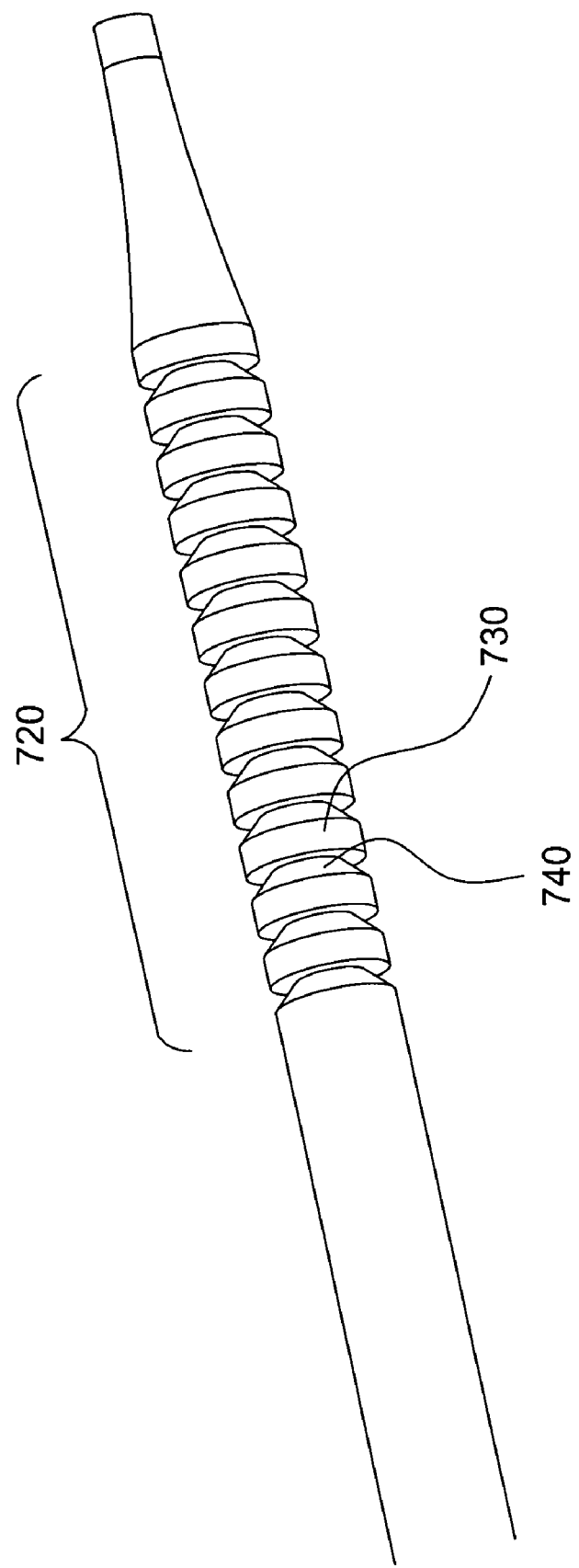
FIG. 12 is a fragmentary perspective view of another embodiment of a reflective cMUT IVUS catheter.

Another embodiment of a reflective cMUT IVUS catheter is shown in FIG. 12. Modular series 720 consists of single-sided cMUT rings 730 and single sided sonic mirrors 740. The one-sided configuration of FIG. 12 is potentially easier and relatively less inexpensive to produce in large quantities than the embodiment depicted in FIG. 5, and allows for particularly flexible catheter-mounted probes due to the smaller required thickness of the elements. For example, the elements (modules) of the illustrated alternative embodiment have a thickness of between 0.005 and 0.050 inches, and in some embodiments more particularly between 0.007 and 0.020 inches. By design, the axial image planes are equidistant from each other. In the previously described two-sided embodiment, the cMUT ring and mirror are each manufactured at specific widths in order to assure completely equidistant image planes.

Figure 13:
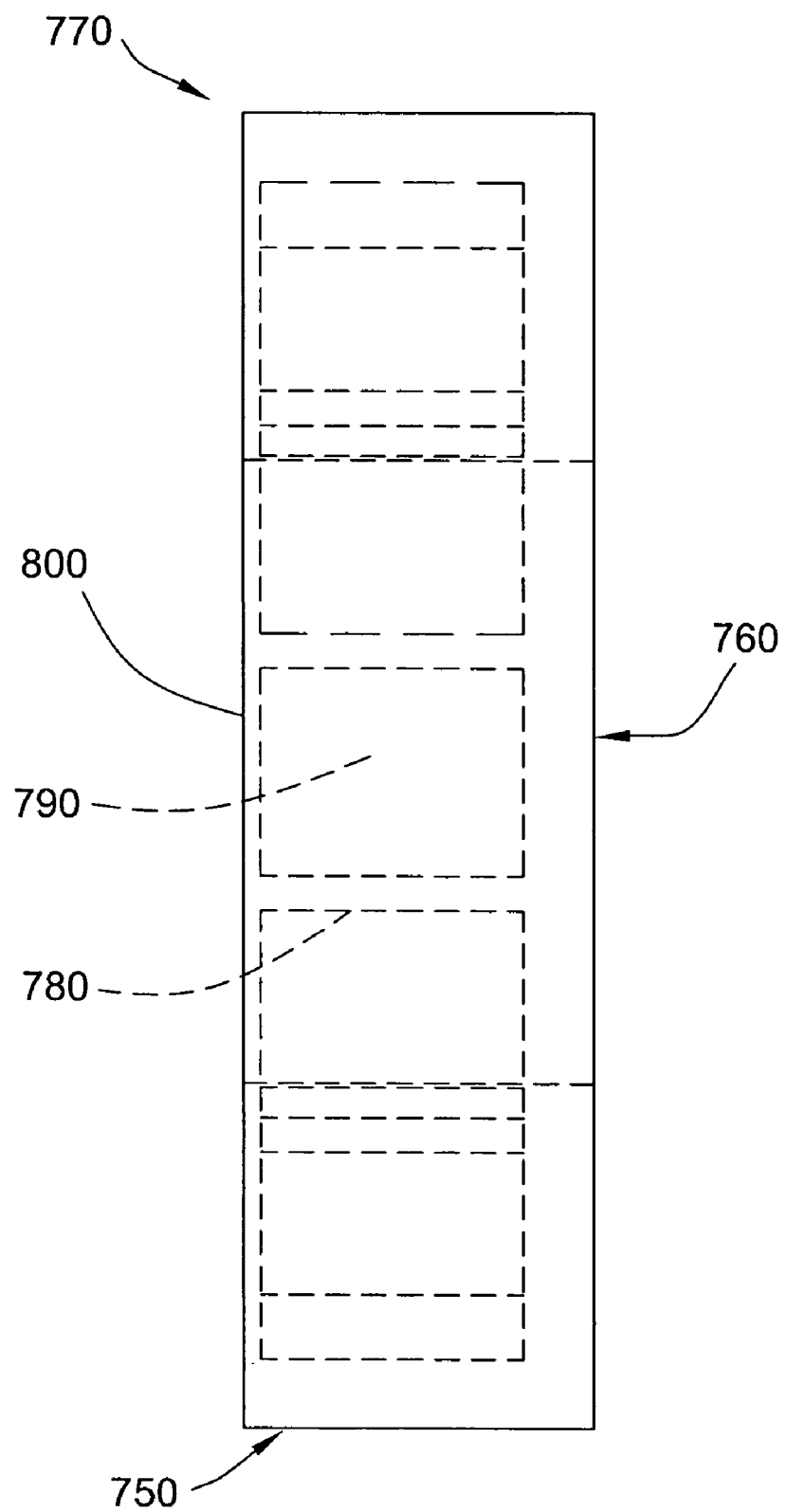
FIG. 13 is a side view of another embodiment of a modular cMUT ring.

FIG. 13 illustrates a one-sided cMUT ring 770 having an outer circumferential wall 750, an inner circumferential wall (not visible in this figure) and a series of internal walls 780. There is also a back wall 760, because there are no membranes on the back side of the ring 770. Also shown are a cavity 790 and a corresponding membrane 800.

Figure 14:
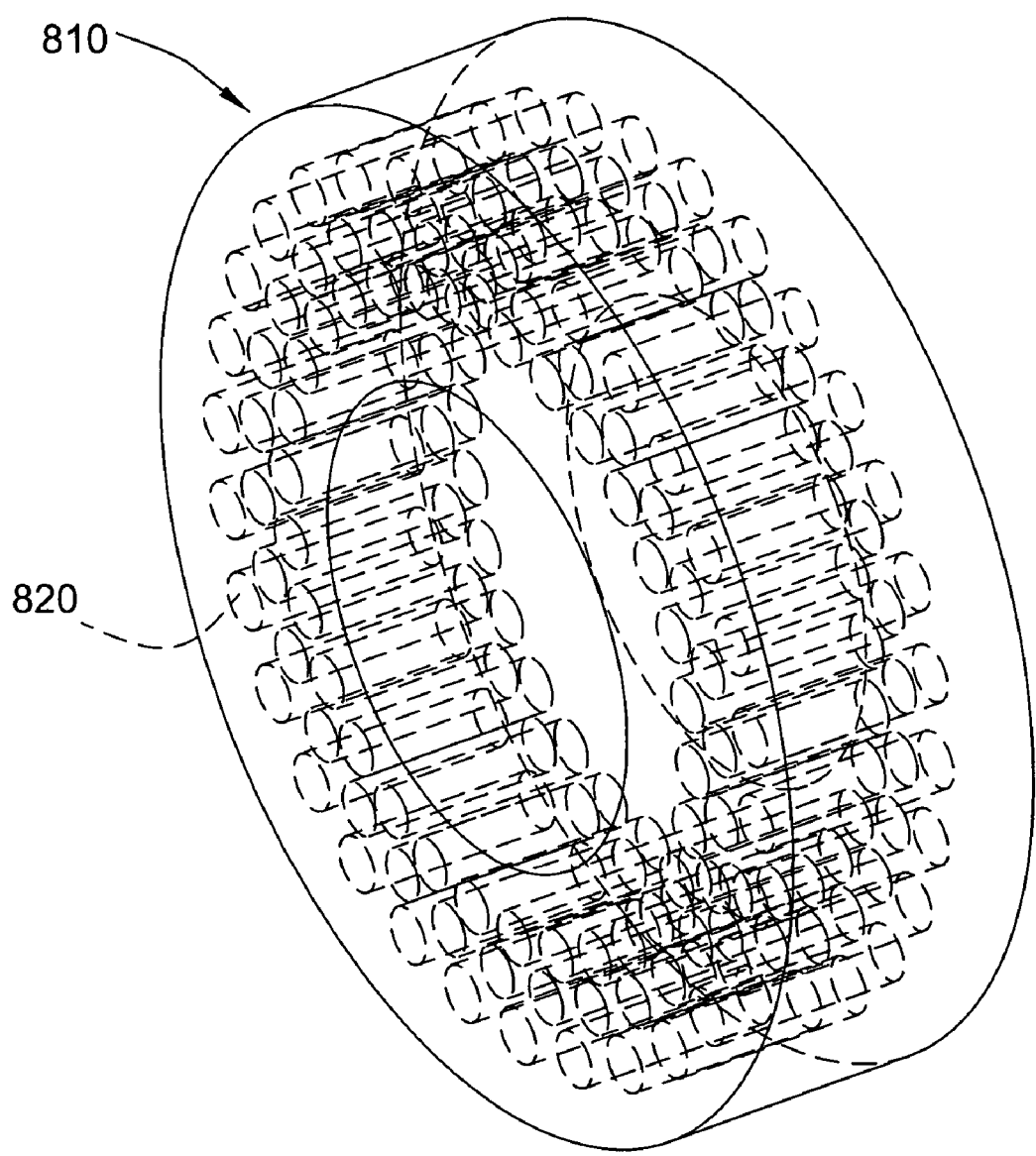
FIG. 14 is a perspective view of another embodiment of a modular cMUT ring with a plurality of drums.

FIG. 14 depicts an alternative embodiment of a drum pattern on a cMUT ring. The cMUT ring diameter is, by way of example, similar to the cMUT rings in the previously described embodiments of a cMUT ring (for example, about 0.038 inches in some embodiments), but in this case, the drum diameters may be smaller. By way of example and not limitation, the drum diameters in this embodiment are approximately 0.002 inches—compared to 0.006 inches in the previously described embodiments including a single circle of transducer elements. In the illustrated embodiment of FIG. 14, the drum pattern consists of three circles of 30 drums 820 for a total of 90 drums. In other embodiments, the outer row can be more densely/efficiently filled (than the illustrated embodiment in FIG. 14) so that it has a greater number of drums than the inner row. It will be appreciated that the drums may be of any suitable size and any suitable quantity of drums are disposed on the cMUT ring in any suitable pattern in accordance with alternative embodiments.

Figure 15:
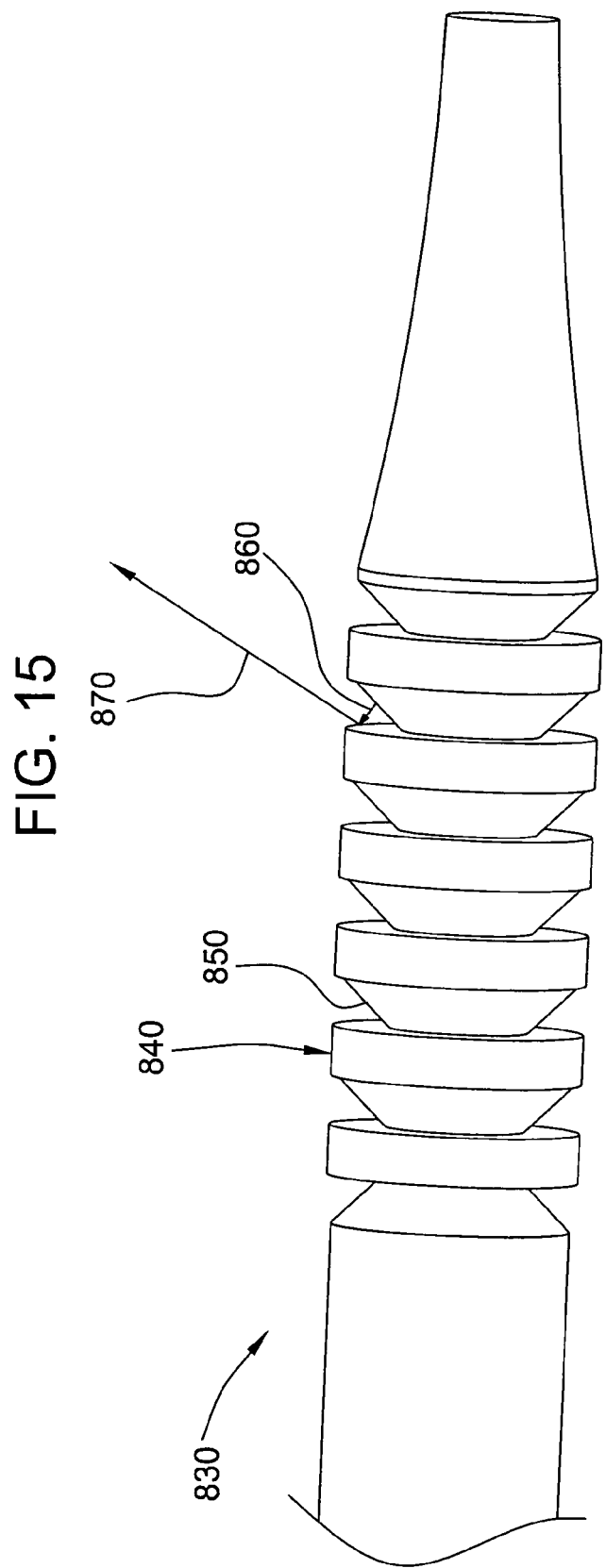
FIG. 15 is a fragmentary side view of another embodiment of a reflective cMUT IVUS catheter suitable for side and forward viewing.

FIG. 15 shows a reflective cMUT IVUS catheter that delivers and receives ultrasonic waves in angular paths so that it can be used for both side-viewing and forward-viewing. Forward viewing can be especially useful in applications such as chronic total occlusions and the placement of a guidewire into structures of the heart, such as the coronary sinus, a pulmonary vein, or defects such as a patent foramen ovale (PFO) or an atrial septal defect (ASD). In the chronic total occlusion application, the guidewire lumen can be used to deliver a guidewire through the occlusion while the catheter images in the forward direction to assure that the guidewire is not passing through the wall of the artery. In this type of catheter, it may be desirable to have the proximal guidewire port located outside of the patient in the manifold so that multiple guidewires can be exchanged as the examination/procedure progresses.

Figure 16:
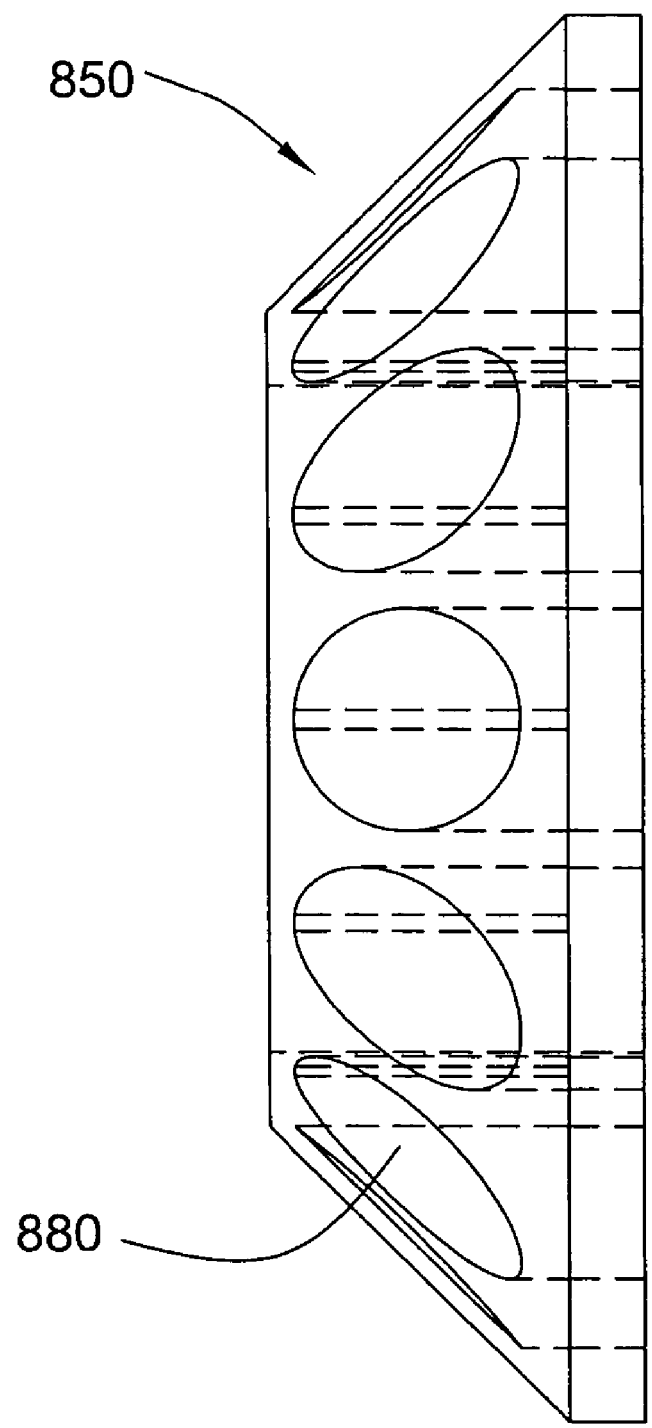
FIG. 16 is a side view of another embodiment of a modular cMUT ring.

Another example of a forward looking application is in Intracardiac Echocardiography (ICE). For example, a catheter can be placed so that the tip is in the right atrium and, while forward-viewing, the coronary sinus can be identified (by either blood flow or tissue imaging) and a guidewire can be delivered into the coronary sinus. This allows for the subsequent delivery of bi-ventricular pacing leads. In addition, the catheter is, for example, combined with a steering mechanism, which allows the tip to be aimed in the desired direction. A similar system is used for placing a guidewire into a pulmonary vein, a PFO, ASD or other heart structures or defects. The distal end 830 of a side and forward viewing reflective cMUT IVUS catheter comprises flat sonic mirrors, e.g., sonic mirror 840 and cMUT rings 850 having a beveled face. The beveled face is shown in FIG. 16. The membranes, such as membrane 880, are disposed at any suitable angle, including but not limited to an angle such as 45°. As shown in FIG. 15, emitted ultrasonic waves 860 reflect off the sonic mirror surface in a reflective angle that has both side and forward components. A reflected wave 870 is therefore potentially able to penetrate tissue that is located both to the side and forward relative to the catheter.

Figure 17:
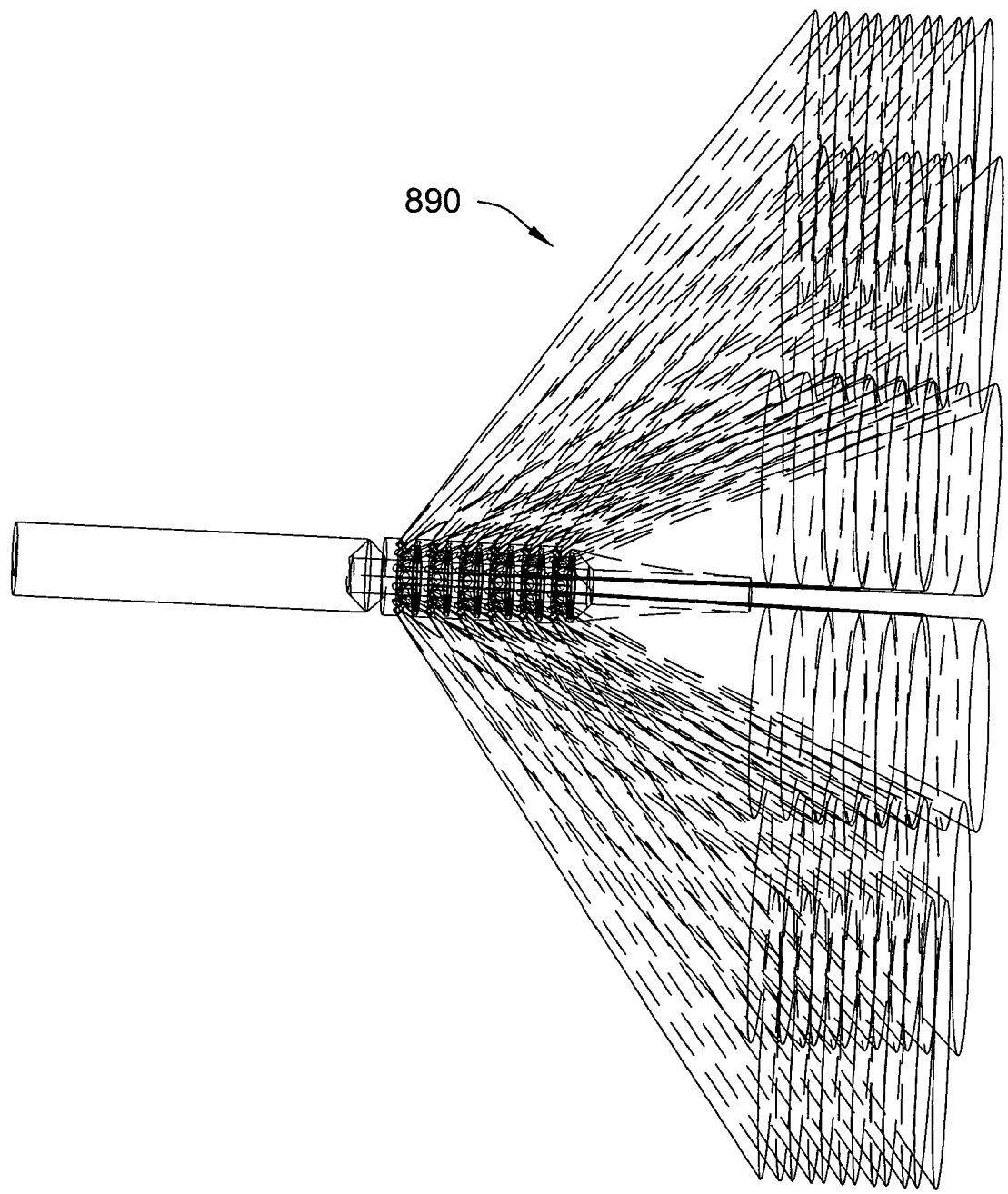
FIG. 17 is a side view of the reflective cMUT catheter of FIG. 15 showing the shape of the sonic field during the firing of a selective number of cMUT rings.

FIG. 17 shows a catheter that is firing more than one of its cMUT rings. The ultrasound field 890 potentially has a funnel shape directed forward relative to the catheter, while still imaging tissue to the side.

Figure 18:
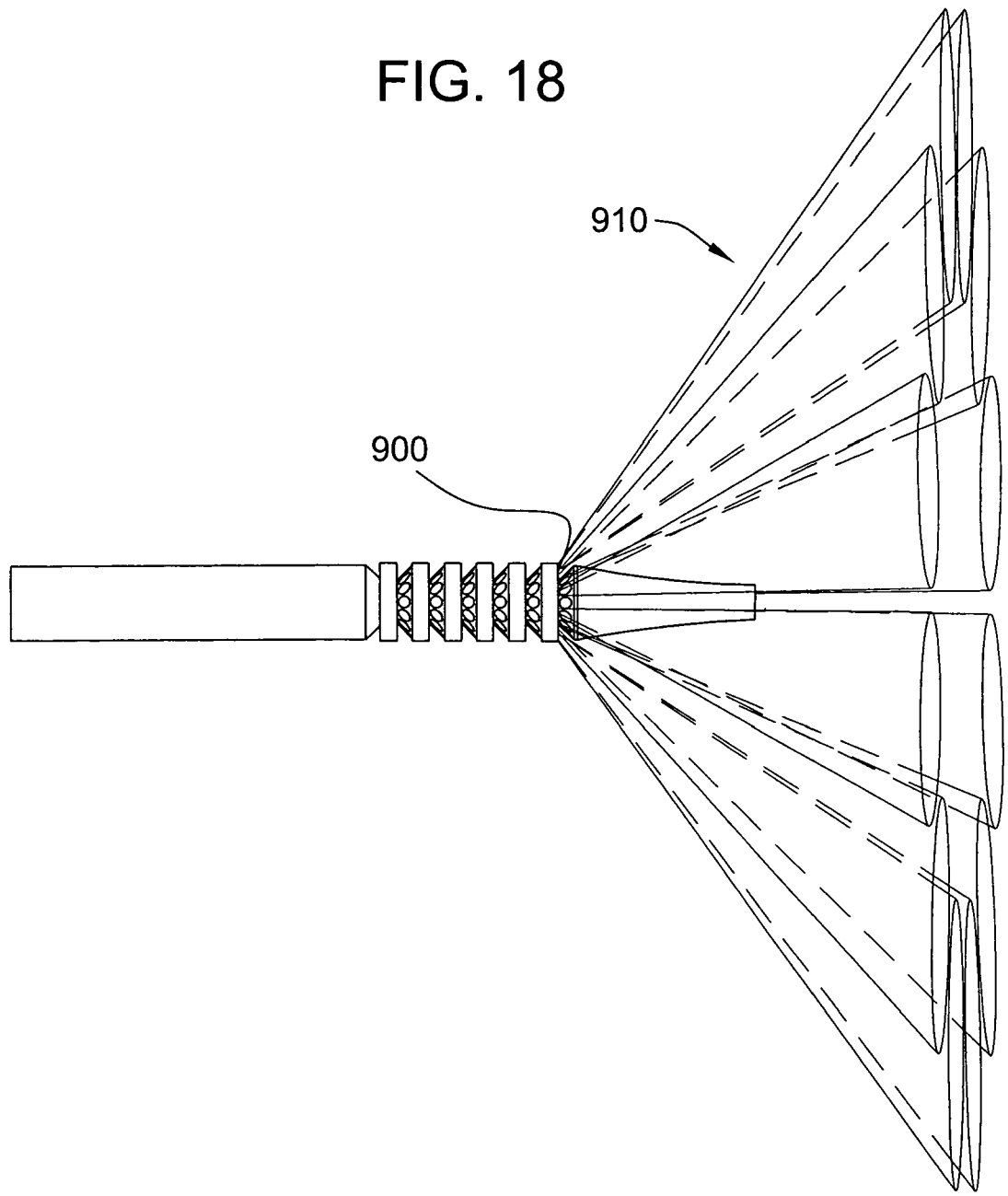
FIG. 18 is another side view of the reflective cMUT catheter of FIG. 15 showing the firing of the foremost cMUT ring only.

In FIG. 18, the exemplary catheter is constructed such that it has a distal cMUT ring 900 that can fire independently of the other cMUT rings. The forward-viewing ultrasound field 910 is suitable for a forward-viewing application, such as total occlusions. The distal cMUT ring 900 is made differently from the other cMUT rings on the catheter, for example, with differing membrane constructions, so that it vibrates at a lower frequency, and thus, penetrates deeper into the tissue. An exemplary frequency is chosen from within the range of 2 MHz to 20 MHz, for coronary CTO applications. It will be appreciated that the catheter may fire any suitable number of rings at a time, including all of the rings at or approximately at the same time, to image tissue disposed near the front and/or the side of the catheter.

It is noted that cMUT membranes may be any suitable size including as thin as only a few microns, although for purposes of explanation, they may be shown larger than scale in the Figures.

Figure 19:
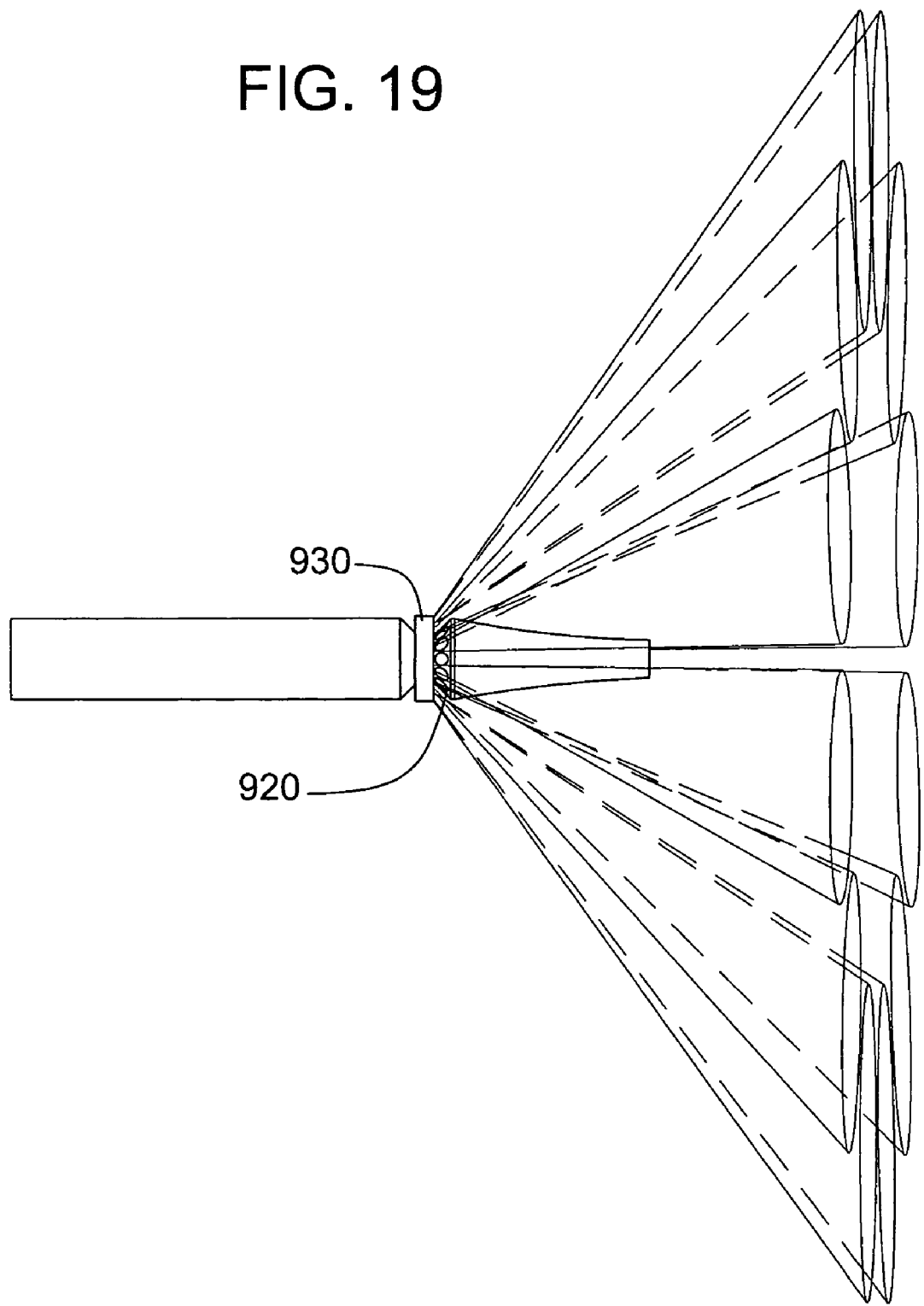
FIG. 19 is another embodiment of a reflective cMUT IVUS catheter particularly suitable for forward looking procedures.

FIG. 19 depicts an embodiment of a side-viewing/forward-viewing catheter that only has one cMUT ring 920 and one mirror 930, and is preferably used for forward-viewing. Because of the relatively short length of the imaging section of this catheter, the distal end is potentially very flexible. The catheter embodiment depicted in FIG. 19 is ideal for forward-viewing during a chronic total occlusion procedure. A guidewire or a series of guidewires are used down the guidewire lumen of the catheter while forward-viewing the occlusion. As the guidewire penetrates further, the catheter is advanced along behind the guidewire with relative ease because of its excellent flexibility and tapered tip.

The sonic mirrors of the cMUT devices described herein are, for example, constructed of a very dense material which serves as an efficient reflector of ultrasound. In addition, it is desirable in some embodiments that the sonic mirrors have a very smooth surface with surface imperfections no more than one-tenth of an ultrasound wavelength. An example of an ideal material is stainless steel, which has an acoustic impedance significantly higher than blood or saline, and can be polished to a mirror-smooth surface. In addition, stainless steel is a common material used in intravascular catheters. The nitride layer of the cMUT drum is generally less than a wavelength thick, so it does not serve as a true acoustic medium itself. It will be appreciated that the sonic mirror may be constructed of any suitable material.

Figure 20:
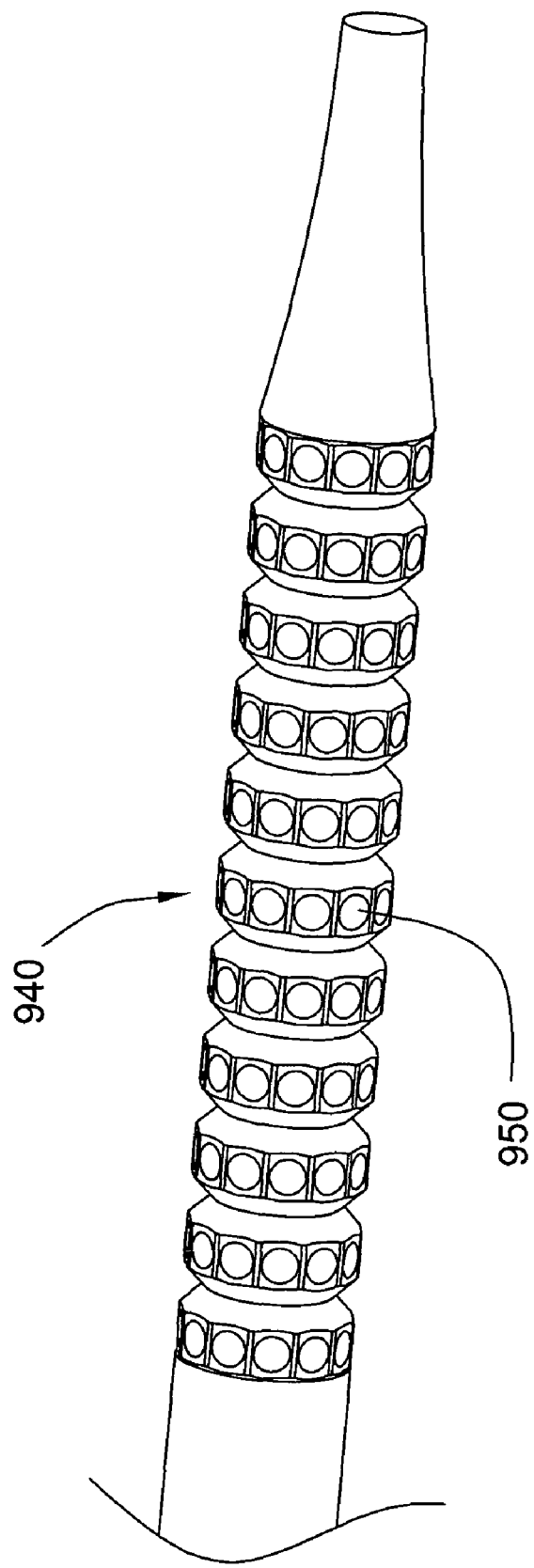
FIG. 20 is a fragmentary perspective view of an embodiment of a direct cMUT IVUS catheter.

FIG. 20 shows another embodiment of a cMUT IVUS catheter without mirrors, which need not utilize a reflective surface on the catheter. Each cMUT ring 940 has a series of radially oriented drums with membranes, e.g., membrane 950. The membranes are directly side-firing, and the dimensions of the elements and the catheter itself are, for example, on the same order as previously discussed reflective cMUT IVUS embodiments.

Figure 23:
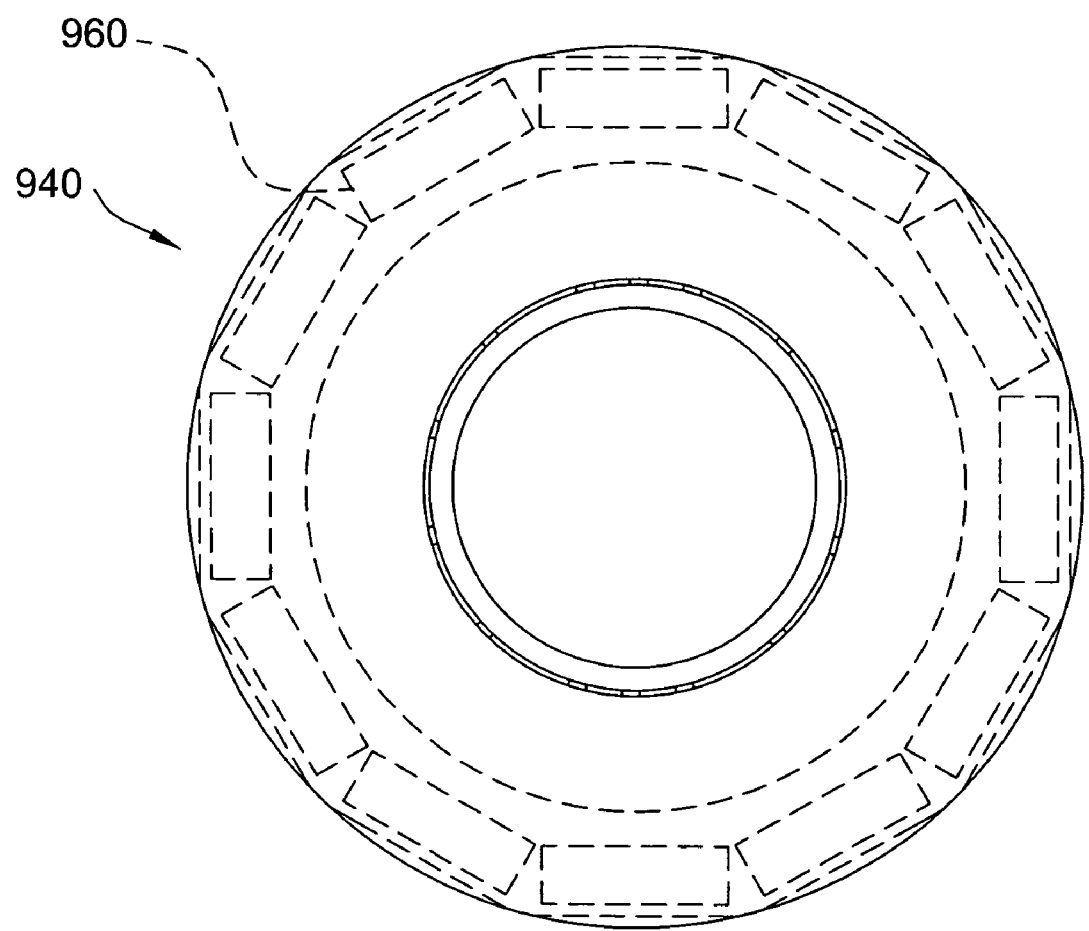
FIG. 23 is a cross-sectional view of an embodiment of a cMUT ring shown with the direct cMUT IVUS of FIG. 20.

Turning to FIG. 23, a cross-section of the cMUT ring of this direct cMUT IVUS catheter demonstrates the arrangement of the drums, e.g., drum 960 along the outer portion of the cMUT ring 940. In this embodiment, the conductive stripes in the inner diameter of the cMUT ring 940 are, for example, similar to the cMUT rings of the reflective cMUT IVUS catheters. However, the conductive paths between the conductive stripes and the membranes 950 are carefully configured so that they do not contact the conductive paths of another cMUT ring. In further embodiments, the conductive paths are formed internally of the cMUT ring. In FIG. 23, the surface of the membranes 950 is flat and does not exactly follow the rounded, continuous circumferential contour of the outer surface of the cMUT ring 940. Alternatively, the cMUT ring can be formed so that the membranes follow exactly the circumferential contour and maintain a consistent thickness throughout.

Figure 21:
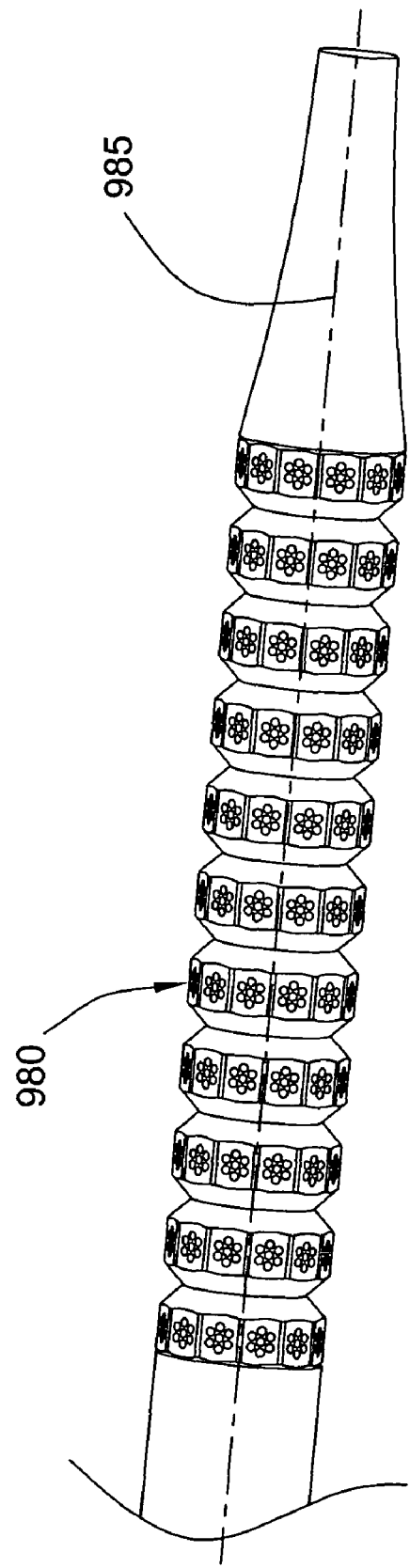
FIG. 21 is another embodiment of a direct cMUT IVUS catheter.
Figure 22:
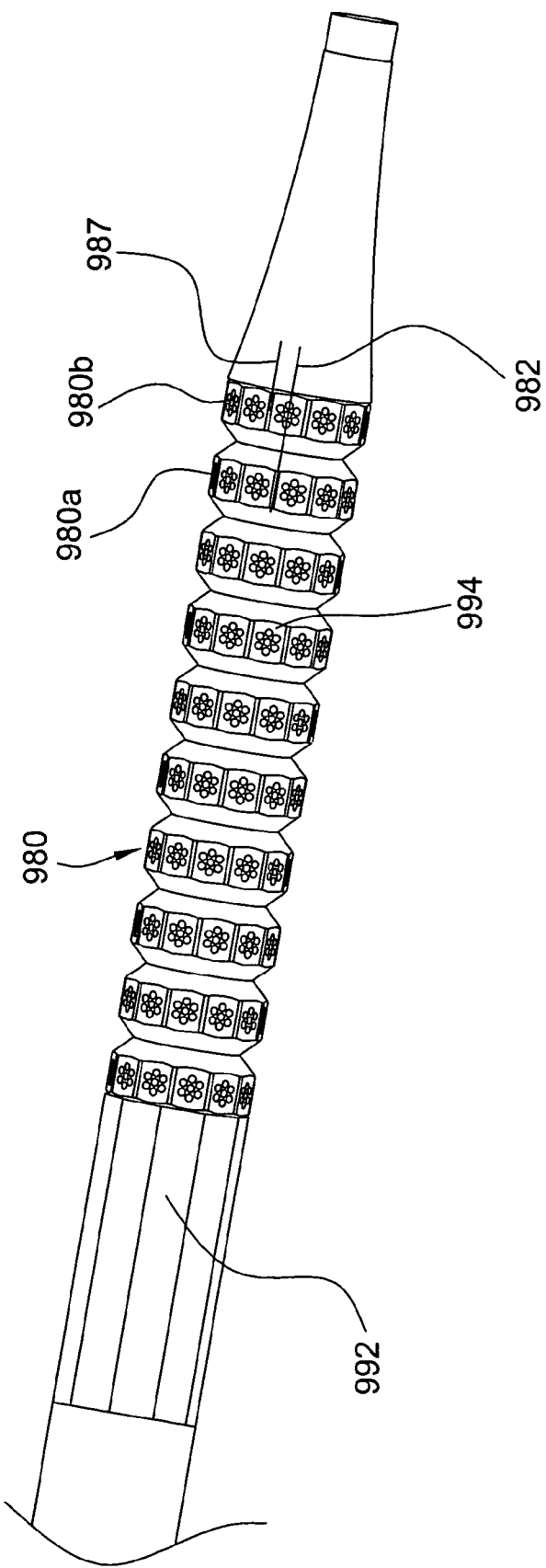
FIG. 22 is another embodiment of a direct cMUT IVUS catheter, the catheter having staggered drum orientation angles.

FIGS. 21 and 22 depict additional embodiments of a direct cMUT IVUS catheter similar to the embodiment described in FIG. 20. In place of the single drum in each of the dodecahedral sides, there is instead an array of seven smaller drums. The seven drums create a circular array. It will be appreciated that any suitable number of smaller drums may form the array. Furthermore, in other embodiments, the array is rectangular, a parallelogram, an arrow shape, or any other suitable shape. FIGS. 21 and 22 differ by the orientation between adjacent cMUT rings. In FIG. 21, all of the rings 980 have the same circumferential orientation. Contour line 985 is aligned for all rings. In FIG. 22, the orientation of each consecutive ring is staggered, in this case, by 15°. First contour line 987 for first ring 980*b* is 15° from second contour line 982 of second ring 980*a*. In this manner, a more complex ultrasonic field may be created to add more detail to the imaging data. It will be appreciated that the rings may be staggered at any suitable angle relative to one another.

Referring again to FIG. 22, some embodiments comprise integrated circuits to communicate with and/or control the transducer elements. The integrated circuits, in addition to reducing the number of wires along the length of the catheter, also potentially carry out signal amplification and filtering as well as controlling firing sequences of the sets of transducer elements on the device. As shown, the integrated circuits 992 are, for example, disposed near the distal end of the catheter shaft near the cMUT rings, e.g., ring 980. The integrated circuits 992 selectively multiplex/route the signals from the transducer rings 980 to a substantially smaller number of wires running along the catheter to its proximal connector interface.

In the illustrative embodiment, there are, for example, ten integrated circuits 992, and each circuit 992 is disposed as a respective one of the ten angled surfaces on the catheter shaft. Each of the ten integrated circuits 992 communicates with one of the ten cMUT rings 980. It will be appreciated that a suitable number of integrated circuits are disposed at suitable locations on the catheter to communicate with any suitable number of cMUT rings and/or drums. For example, in other embodiments, integrated circuits are mounted upon each ring, e.g., ring 980 to communicate with the corresponding membrane(s) on the respective ring.

Figure 24:
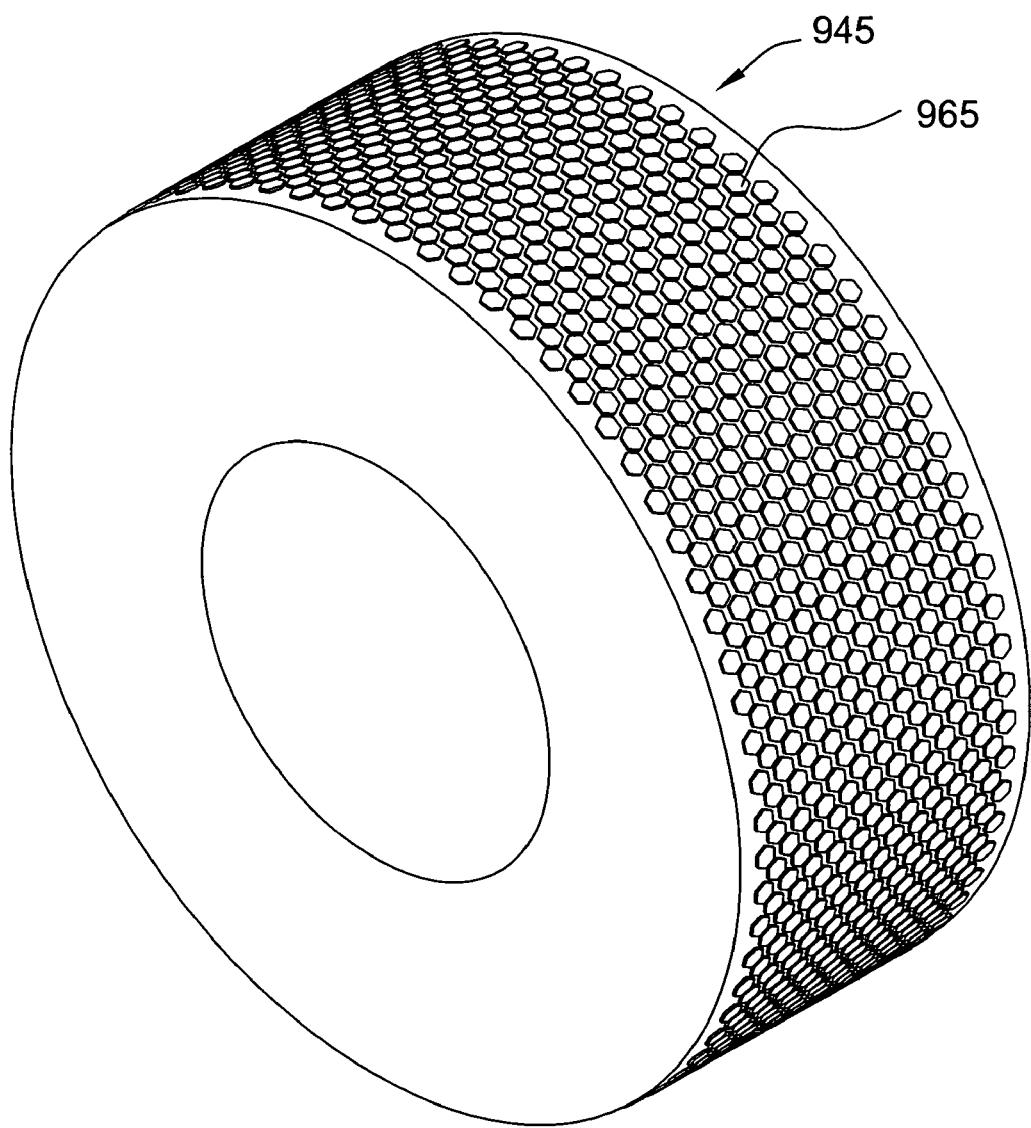
FIG. 24 is another embodiment of a cMUT ring for a direct cMUT IVUS catheter.

Another embodiment of a cMUT ring 945 for a direct cMUT IVUS catheter is presented in FIG. 24. In this embodiment, a honeycomb pattern of drums, e.g., drum 965, are arrayed around the circumference of the cMUT ring 945. In this specific configuration there are alternating rows of eleven and ten drums. With a total of 144 rows, there are a total of 1512 drums. The necessary multiplexers may be cylindrically configured within the substrate of the cMUT ring 945 using conventional semi-conductor foundry fabrication techniques.

In addition to rings, the cMUT modules are configured in other suitable shapes that allow for a more non-symmetric catheter cross section. These include, but are not limited to, elliptical cross-sections, teardrop cross-sections and rectangular cross-sections. The membranes of the cMUT rings are not limited to the circular shape or honeycomb pattern presented here, but can also have a variety of other smooth and polygonal shapes. In addition, it will be appreciated that a suitable number of drums are arranged in a suitable pattern in accordance with various alternative embodiments.

Furthermore, with regard to the mirror/reflectors, in accordance with various embodiments, instead of the beveled angle on the mirrors or cMUT rings, the mirrors and cMUT rings may be other suitable shapes including, but not limited to, concave or convex shapes.

It will also be appreciated that the drum membrane is potentially disposed at any suitable angle relative to a longitudinal axis of the catheter. By way of example and not limitation, the angle may be between 5° and 85°, between 25° and 65°, or between 40° and 50°. Similarly, the sonic mirror may have a surface for reflecting ultrasonic waves that is disposed at any of a wide range of suitable angles relative to the longitudinal axis of the catheter.

Besides intravascular ultrasound, other types of ultrasound catheters can be made using the teachings provided herein. By way of example and not limitation, other suitable types of catheters include non-intravascular intraluminal ultrasound catheters, intracardiac echo catheters, laparoscopic, and interstitial catheters.

Recitation of ranges of values herein are merely intended to serve as a shorthand method of referring individually to each separate value falling within the range, unless otherwise indicated herein, and each separate value is incorporated into the specification as if it were individually recited herein.

Any references, including publications, patent applications, and patents, cited herein are hereby incorporated by reference to the same extent as if each reference were individually and specifically indicated to be incorporated by reference and were set forth in its entirety herein (including any references contained therein).

Illustrative embodiments of a cMUT-based probe are described herein. Variations of the disclosed embodiments will be apparent to those of ordinary skill in the art in view of the foregoing illustrative examples. Those skilled in the relevant art will employ such variations as appropriate, and such variations, embodied in alternative embodiments, are contemplated within the scope of the disclosed invention. The invention is therefore not intended to be limited to the examples described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An ultrasound catheter for insertion into a vasculature, the catheter comprising:
    an elongate flexible shaft having a proximal end and a distal end;
    a capacitive microfabricated ultrasonic transducer device mounted on the shaft near the distal end, wherein the transducer comprises a drum structure having a membrane disposed such that a face of the membrane is oriented to emit ultrasound waves; and
    a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer;
    wherein the transducer and reflector are oriented to facilitate forward viewing; and
    wherein the face of the membrane is skewed to emit the ultrasound waves other than along a longitudinal axis of the catheter.

2. The ultrasound catheter of claim 1 wherein the skew angle is greater than 5 degrees and less than 85 degrees.

3. The ultrasound catheter of claim 1 wherein the skew angle is greater than 25 degrees and less than 65 degrees.

4. The ultrasound catheter of claim 1 wherein the skew angle is greater than 40 degrees and less than 50 degrees.

5. An ultrasound catheter for insertion into a vasculature, the catheter comprising:
- an elongate flexible shaft having a proximal end and a distal end;
- a capacitive microfabricated ultrasonic transducer device mounted on the shaft near the distal end, wherein the transducer comprises a drum structure having a membrane disposed such that a face of the membrane is oriented to emit ultrasound waves;
- a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer; and
- an integrated circuit disposed on the flexible shaft and coupled to the transducer, the integrated circuit performing at least a signal multiplexing function on signals corresponding to received ultrasound echoes.

6. The ultrasound catheter of claim 5 wherein the reflective surface is oriented to support side viewing.

7. The ultrasound catheter of claim 6 wherein the membrane is oriented to emit the ultrasound waves substantially along a longitudinal axis of the catheter.

8. The ultrasound catheter of claim 5 wherein the flexible shaft comprises a guidewire lumen.

9. The ultrasound catheter of claim 8 wherein the guidewire lumen terminates at openings at the proximal end and distal end of the flexible shaft.

10. An ultrasound catheter for insertion into a vasculature, the catheter comprising:
- an elongate flexible shaft having a proximal end and a distal end;
- a capacitive microfabricated ultrasonic transducer device mounted on the shaft near the distal end, wherein the transducer comprises a drum structure having a membrane disposed such that a face of the membrane is oriented to emit ultrasound waves;
- a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer; and
- at least a first and a second sonic reflector and a flex point disposed between the first and second sonic reflectors.

11. An ultrasound catheter for insertion into a vasculature, the catheter comprising:
- an elongate flexible shaft having a proximal end and a distal end;
- a capacitive microfabricated ultrasonic transducer device mounted on the shaft near the distal end, wherein the transducer comprises a drum structure having a membrane disposed such that a face of the membrane is oriented to emit ultrasound waves, wherein the transducer is formed within a ring, and wherein the drum structure is disposed on only one side of the ring; and
- a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer.

12. An ultrasound catheter for insertion into a vasculature, the catheter comprising:
- an elongate flexible shaft having a proximal end and a distal end;
- a capacitive microfabricated ultrasonic transducer device mounted on the shaft near the distal end, wherein the transducer comprises a drum structure having a membrane disposed such that a face of the membrane is oriented to emit ultrasound waves, wherein the transducer is formed within a ring that comprises a plurality of drum structures and wherein at least one of the plurality of drums is disposed on a first face of the ring and configured to emit ultrasound waves proximally in a direction substantially parallel to a longitudinal axis of the catheter and at least one of the plurality of drum structures is disposed on a second face of the ring and configured to emit ultrasound waves distally in a direction substantially parallel to the longitudinal axis of the catheter; and
- a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer.

13. An ultrasound catheter for insertion into a vasculature, the catheter comprising:
- an elongate flexible shaft having a proximal end and a distal end;
- a capacitive microfabricated ultrasonic transducer device mounted on the shaft near the distal end, wherein the transducer comprises a drum structure having a membrane disposed such that a face of the membrane is oriented to emit ultrasound waves;
- a sonic reflector mounted on the shaft adjacent to and separate from the drum structure such that the sonic reflector is movable relative to the transducer about a flex point, the sonic reflector comprising a reflective surface and positioned such that the reflective surface redirects the ultrasonic waves to and from the transducer; and
- a conductive bridge disposed on a ring comprising the transducer.

14. An ultrasound catheter for insertion into a vasculature, the catheter comprising:
- an elongate flexible shaft having a proximal end and a distal end;
- a plurality of capacitive microfabricated ultrasonic transducer modules mounted on the shaft near the distal end, and wherein the transducer modules are adapted to permit flexing of the shaft between pairs of the transducer modules, and wherein each of the plurality of transducer modules comprises a plurality of drum structures having a membrane oriented to emit ultrasound waves, and
- a plurality of sonic reflectors mounted on the shaft adjacent to and separate from the plurality of transducer modules in an alternating fashion such that the plurality of sonic reflectors are movable relative to the plurality transducer modules to allow flexing of the shaft, the sonic reflector, each of the plurality of sonic reflectors comprising at least one reflective surface, the reflective surface redirecting the ultrasonic waves to and from the plurality of drum structures of an adjacent transducer module.

15. The ultrasound catheter of claim 14 wherein a flex point is disposed between at least two of the plurality of transducer modules.

16. The ultrasound catheter of claim 14 further comprising a plurality of conductive lines disposed upon the flexible shaft such that the plurality of transducer modules are electrically coupled to the plurality of conductive lines.

17. The ultrasound catheter of claim 14 further comprising integrated circuitry disposed on the flexible shaft and coupled to the transducer modules.

18. The ultrasound catheter of claim 14 wherein the plurality of drum structures of the transducer modules and the reflective surfaces of the plurality of sonic reflectors are oriented to facilitate forward viewing.

19. The ultrasound catheter of claim 14 wherein the plurality of drum structures of the transducer modules and the reflective surfaces of the plurality of sonic reflectors are oriented to facilitate side viewing.

20. The ultrasound catheter of claim 14 wherein the plurality of transducer modules comprises a plurality of sides disposed around respective perimeters of each.

21. The ultrasound catheter of claim 20 further comprising a plurality of edges disposed between the plurality of sides, and wherein adjacent transducer modules are rotated relative to one another such that the edges of the adjacent transducers are skewed in relation to adjacent ones of the transducer modules.

22. The ultrasound catheter of claim 14 wherein the flexible shaft comprises a guidewire lumen.

23. The ultrasound catheter of claim 22 wherein the guidewire lumen extends from a distal port at the distal end to a second port located between 20 and 30 centimeters from the distal port.

24. An ultrasound catheter for insertion into a vasculature, the catheter comprising:
an elongate flexible shaft having a proximal end and a distal end;
a capacitive microfabricated ultrasonic transducer module mounted on the shaft near the distal end, wherein the transducer module comprises a first drum structure having a first membrane disposed such that a first face of the first membrane is oriented substantially perpendicular to a longitudinal axis of the shaft and configured to emit ultrasound waves distally along the length of the shaft and a second drum structure having a second membrane disposed such that a second face of the second membrane is oriented substantially perpendicular to the longitudinal axis of the shaft and configured to emit ultrasound waves proximally along the length of the shaft;
integrated circuitry for performing at least a multiplexing function with regard to signal lines from at least the first and second drum structures of the transducer module;
a first sonic reflector positioned adjacent the first face of the first membrane and in a fixed orientation relative to the first membrane, the first sonic reflector comprising a first reflective surface that redirects the ultrasonic waves emitted to and from the first drum structure; and
a second sonic reflector positioned adjacent the second face of the second membrane and in a fixed orientation relative to the second membrane, the second sonic reflector comprising a second reflective surface that redirects the ultrasonic waves emitted from the second drum structure.

25. The ultrasound catheter of claim 24 wherein the integrated circuitry is mounted directly upon the flexible shaft.

26. The ultrasound catheter of claim 24 wherein the integrated circuitry is integrally formed with the transducer module.

* * * * *